(12) United States Patent
Wharton et al.

(10) Patent No.: US 8,207,211 B2
(45) Date of Patent: Jun. 26, 2012

(54) PHOTOSENSITIZERS FOR TARGETED PHOTODYNAMIC THERAPY

(75) Inventors: Tim Wharton, Bryan, TX (US);
Hariprasad Gali, Edmond, OK (US);
Michael R. Hamblin, Revere, MA (US)

(73) Assignees: The General Hospital Corporation, Boston, MA (US); Lynntech, Inc., College Station, TX (US)

( * ) Notice: Subject to any disclaimer, the term of this patent is extended or adjusted under 35 U.S.C. 154(b) by 1007 days.

(21) Appl. No.: 11/885,241

(22) PCT Filed: Feb. 28, 2006

(86) PCT No.: PCT/US2006/006894
§ 371 (c)(1),
(2), (4) Date: Jul. 23, 2008

(87) PCT Pub. No.: WO2006/093891
PCT Pub. Date: Sep. 8, 2006

(65) Prior Publication Data
US 2009/0076115 A1 Mar. 19, 2009

Related U.S. Application Data

(60) Provisional application No. 60/657,181, filed on Feb. 28, 2005.

(51) Int. Cl.
*A61K 31/403* (2006.01)
*C07D 487/22* (2006.01)
(52) U.S. Cl. ......... 514/410; 548/417; 977/734; 977/904
(58) Field of Classification Search ............... 514/410; 548/417; 977/734, 904
See application file for complete search history.

(56) References Cited

OTHER PUBLICATIONS

Wharton, et al. "New non-ionic, highly water-soluble derivatives of C60 designed for biological compatibility" Tetrahedron Letters, 2001, vol. 42, pp. 5159-5162.*
Tegos et al. "Cationic Fullerenes Are Effective and Selective Antimicrobial Photosensitizers" Chemistry and Biology, 2005, vol. 12, No. 10, pp. 1127-1135.*
Dolmans, D.E., Fukumura, D., and Jain, R.K. (2003). Photody-namic therapy for cancer. Nat. Rev. Cancer 3, 380-387.
Bown, S.B., and Mellish, K.J. (2001). Verepor?n: a milesone in opthalmology and phoodynamic therapy. Expert Opin. Pharmacother. 2, 351-361.
Moan, J., and Peng, Q. (2003). An outline of the hundred-year history of PDT. Anticancer Res. 23, 3591-3600.
Wainwright, M. (1998). Photodynamic antimicrobial chemother-apy (PACT). J. Antimicrob. Chemother. 42, 13-28.
Maisch, T. Szeimies, R.M., Jori, G., and Abels, C. (2004). Photochem. Photobiol. Sci. 3, 907-917 and 30.
Hamblin, M.R., and Hasan, T. (2004) Photodynamic therapy: a new antimicrobial approach to infectious disease? Photo-chem. Photobiol. Sci. 3, 436-450.
Wharton, et al. "New non-ionic, highly water-soluble derivatives of C60 designed for biological compatibility" Tetrahedron Letters, 2001, vol. 42, pp. 5159-5162, the whole document.
Tegos, et al. "Cationic Fullerenses Are Effective and Selective Antimicrobial Photosensitizers" Chemistry & Biology Oct. 2005, vol. 12, pp. 1127-1135, the whole document.
International Search Report for International Application No. PCT/US2006/06894.

* cited by examiner

*Primary Examiner* — Joseph Kosack
(74) *Attorney, Agent, or Firm* — Edwards Wildman Palmer LLP; Peter C. Lauro, Esq.; Nicholas J. DiCeglie, Jr., Esq.

(57) ABSTRACT

The present invention relates to photosensitizer compounds based on functionalized fullerenes useful in targeted photodynamic therapy (PDT), and methods of use thereof.

4 Claims, 21 Drawing Sheets

PHOTOSENSITIZERS FOR TARGETED PHOTODYNAMIC THERAPY

CROSS-REFERENCE TO RELATED APPLICATIONS/PATENTS & INCORPORATION BY REFERENCE

This application is a U.S. national phase application, pursuant to 35 U.S.C. §371, of PCT international application Ser. No. PCT/US06/006894 filed Feb. 28, 2006, designating the United States and published in English on Sep. 8, 2006 as publication WO 2006/093891 A2, which claims priority to U.S. provisional application Ser. No. 60/657,181, filed Feb. 28, 2005. The entire contents of the aforementioned patent applications are incorporated herein by this reference.

Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List, or in the text itself; and, each of these documents or references ("herein-cited references"), as well as each document or reference cited in each of the herein-cited references (including any manufacturer's specifications, instructions, etc.), is hereby expressly incorporated herein by reference.

STATEMENT OF U.S. GOVERNMENT INTEREST

Funding for the present invention was provided in part by the Government of the United States under Grant Nos. R43 CA103268, and R01 AI050875 from the National Institutes of Health. Accordingly, the Government of the United States has certain rights in and to the invention.

BACKGROUND OF THE INVENTION

Photodynamic therapy (PDT) refers to the use of photosensitizing drugs in combination with light for treating medical conditions. The PDT technique has shown promise as a cancer therapy (Dolmans, D. E., Fukumura, D., and Jain, R. K. (2003). Photodynamic therapy for cancer. *Nat. Rev. Cancer* 3, 380-387) and recently has achieved success as a treatment for age-related macular degeneration (Brown, S. B., and Mellish, K. J. (2001). Verteporfin: a milestone in opthalmology and photodynamic therapy. Expert Opin. *Pharmacother.* 2, 351-361). The PDT method uses a compound known as a photosensitizer (PS) which is administered directly (e.g., endoscopically or topically) to an accessible treatment site, or alternatively, is administered systemically and concentrates in a target tissue site within the body of a subject. Subsequent irradiation of the target site with visible light of suitable wavelength generates singlet oxygen, $^1O_2$, within or on the surface of the cells of the treatment site, ultimately leading to cell death. The singlet oxygen is catalytically generated by energy transfer from the PS to oxygen from dissolved $O_2$, which is ubiquitous in the body's tissues. Photodynamic therapy is advantageous compared with other therapies due to its dual selectivity: not only is the PS targeted to the tumor or other lesion, but the light can also be accurately delivered to the affected tissue.

The potential use of a photosensitizer as an effective means of killing microorganisms was first recognized over 100 years ago (Moan, J., and Peng, Q. (2003). An outline of the hundred-year history of PDT. *Anticancer Res.* 23, 3591-3600); however, the possible use of PDT as a treatment for microbial infections is just beginning to be appreciated (Wainwright, M. (1998). Photodynamic antimicrobial chemotherapy (PACT). J. *Antimicrob. Chemother.* 42, 13-28, Maisch, T., Szeimies, R. M., Jori, G., and Abels, C. (2004). Antibacterial photodynamic therapy in dermatology. *Photochem. Photobiol. Sci.* 3, 907-917 and 30. Hamblin, M. R., and Hasan, T. (2004). Photodynamic therapy: a new antimicrobial approach to infectious disease? *Photo-chem. Photobiol. Sci.* 3, 436-450). For decades, antibiotics have been the first line of defense against microorganisms. Of great concern in current medical practice is the proliferation of infectious microbes that display multiple antibiotic resistance, and hence are not killed by existing antibiotics alone or in combination. Accordingly, there is a great unmet need to develop new antimicrobial agents to which microbes are not easily able to develop resistance. In this regard, it is envisioned that treatment of infections with PDT holds great promise as an alternative or adjunct to traditional antibiotic therapy because organisms are unlikely to develop resistance to a killing mechanism based on bombardment of the pathogens with reactive oxygen species.

Given the urgent need for new antimicrobial agents, it would be desirable to develop PS compounds that are effective at killing a broad range of microbes such as bacteria, fungi and yeast but are not harmful to the cells of a mammalian subject receiving antimicribial PS therapy.

SUMMARY OF THE INVENTION

The invention relates to the development and use of a new class of photosensitizing molecules for PDT. It has now been demonstrated that cationic fullerene embodiments functionalized with one, two, or three pyrrolidinium groups, after a short incubation followed by illumination with white light, have a broad-spectrum antimicrobial activity and can rapidly kill more than 99.99% of bacterial and fungal cells.

In this invention, fullerene molecules, e.g., $C_{60}$, $C_{70}$, $C_{74}$, $C_{76}$, $C_{78}$, $C_{80}$, $C_{82}$, $C_{84}$, higher fullerenes and their functionalized derivatives, have been modified to include a variety of properties needed for application of PDT to microorganisms. This was achieved by controlling hydrophobicity, molecular charge, and water solubility of the carbon nanomaterial specifically to target microbial species preferentially over other types of cells for PDT. A positive charge on some embodiments allows the fullerenes to bind to cells and overcome microbial permeability barriers. Cationic fullerenes in particular perform better as antimicrobial photosensitizers than the widely employed antimicrobial photosensitizer toluidine blue O. Accordingly, cationic fullerene-mediated photodynamic therapy may find significant application in the treatment of a wide variety of conditions, such as for example, localized infections in wounds, burns, and mucus membranes.

More particularly, in one embodiment the present invention relates to compositions comprising a functionalized fullerene, wherein the wherein the functionalized fullerene comprises a fullerene core ($C_n$) where n is an even integer greater than or equal to 60, and at least one functional group bonded to at least one carbon atom of the fullerene core.

Some embodiments are based on hydrophilic cationic fullerene derivatives. Other embodiments are hydrophilic neutral fullerene derivatives.

Fullerene derivatives of the invention are suitable for the treatment of a variety of bacterial, viral, and fungal infections. Accordingly, in another embodiment, the invention relates to a method for providing antimicrobial therapy, which includes administering an effective amount of a functionalized fullerene species to a subject in need thereof. The fullerene species can be any one of the compounds described herein. The method includes directing light onto the administered fullerene species to produce a cytotoxic species; and killing microbial cells associated with or proximal to the fullerene species by reaction with the cytotoxic species.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting examples and with reference to the accompanying drawings in which.

DETAILED DESCRIPTION OF THE INVENTION

I. Definitions

Figure 1:
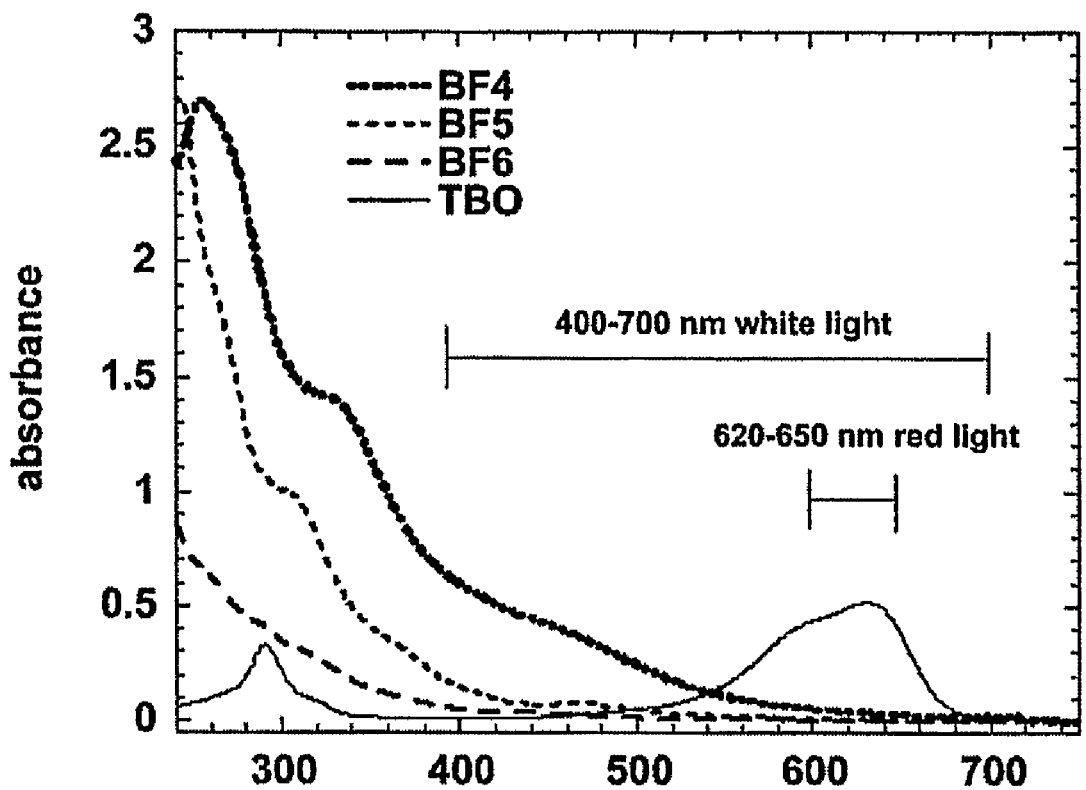
FIG. 1 is a graph showing UV-Visible absorption spectra of common photosensitizer toluidine blue O (TBO) and of derivatized fullerenes (CI1-3) prepared in accordance with the invention.

In order that the invention may be more readily understood, certain terms are first defined and collected here for convenience. Other definitions appear in context throughout the application.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 30 or fewer carbon atoms in its backbone (e.g., $C_1$-$C_{30}$ for straight chain, $C_3$-$C_{30}$ for branched chain), preferably 26 or fewer, and more preferably 20 or fewer. Likewise, certain cycloalkyls have from 3-10 carbon atoms in their ring structure, and more preferably have 3, 4, 5, 6 or 7 carbons in the ring structure.

Moreover, the term alkyl as used throughout the specification and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and most preferably from one to four carbon atoms in its backbone structure, which may be straight or branched-chain.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like.

Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "chiral" refers to molecules which have the property of non-superimposability of the mirror image partner, while the term "achiral" refers to molecules which are superimposable on their mirror image partner.

The term "enantiomers" refers to two stereoisomers of a compound which are non-superimposable mirror images of one another. An equimolar mixture of two enantiomers is called a "racemic mixture" or a "racemate."

The term "halogen" designates —F, —Cl, —Br or —I.

The term "haloalkyl" is intended to include alkyl groups as defined above that are mono-, di- or polysubstituted by halogen, e.g., fluoromethyl and trifluoromethyl.

The term "hydroxyl" means —OH.

The term "heteroatom" as used herein means an atom of any element other than carbon or hydrogen. Preferred heteroatoms are nitrogen, oxygen, sulfur and phosphorus.

The term "isomers" or "stereoisomers" refers to compounds which have identical chemical constitution, but differ with regard to the arrangement of the atoms or groups in space. Furthermore the indication of stereochemistry across a carbon-carbon double bond is also opposite from the general chemical field in that "Z" refers to what is often referred to as a "cis" (same side) conformation whereas "E" refers to what is often referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

The term "obtaining" as in "obtaining the fullerene derivative" is intended to include purchasing, synthesizing or otherwise acquiring the fullerene derivative (or indicated substance or material).

A "photosensitizer" or "photosensitive material" is defined herein as a material, element, chemical, solution, compound, matter, or substance which is sensitive, reactive, receptive, or responsive to light energy. The term can refer to a photoactivatable fullerene compound, or a precursor thereof, that produces a reactive species (e.g., oxygen) having a phototoxic effect on a microbe or infected cell.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "sulfhydryl" or "thiol" means —SH.

The term "subject" refers to animals such as mammals, including, but not limited to, primates (e.g., humans), cows, sheep, goats, horses, dogs, cats, rabbits, rats, mice and the like. In certain embodiments, the subject is a human.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited are not changed by the presence of more than that which is recited, but excludes prior art embodiments.

Unless otherwise defined, all technical and scientific terms used herein have the same meaning as commonly understood by one of ordinary skill in the art to which this invention belongs. In case of conflict, the present application, including definitions will control.

II. Compositions of the Invention

The present invention provides photodynamic compositions for PDT. PDT employs photoactivatable compounds known as photosensitizers to selectively target and destroy cells. Therapy involves delivering visible light of the appropriate wavelength to excite the photosensitizer molecule to the excited singlet state. This excited state can then undergo intersystem crossing to the slightly lower energy triplet state, which can then react further by one or both of two pathways, known as Type I and Type II photoprocesses (Ochsner (1997) J Photochem Photobiol B 39:1-18). The Type I pathway involves electron transfer reactions from the photosensitizer triplet to produce radical ions that can then react with oxygen to produce cytotoxic species such as superoxide, hydroxyl and lipid derived radicals. The Type II pathway involves energy transfer from the photosensitizer triplet to ground state molecular oxygen (triplet) to produce the excited state singlet oxygen, which can then oxidize many biological molecules such as proteins, nucleic acids and lipids, and lead to cytotoxicity.

Functionalized Fullerenes as Photosensitizers

The therapeutic compositions of the invention comprise novel photosensitizer compounds for PDT based on functionalized fullerene molecules. Without being bound by theory, it is believed that the functionalized fullerene molecules of the invention function through the Type I pathway described herein above.

More particularly, the invention relates to fullerenes, e.g., $C_{60}$, $C_{70}$, $C_{74}$, $C_{76}$, $C_{78}$, $C_{80}$, $C_{82}$, $C_{84}$, higher fullerenes and their functionalized derivatives. Buckminsterfullerenes, also known as fullerenes or, more colloquially, "buckyballs," are cage-like molecules consisting essentially of $sp^2$-hybridized carbons. Fullerenes were first reported by Kroto et al., Nature (1985) 318:162. Fullerenes are the third form of pure carbon, in addition to diamond and graphite. Typically, fullerenes are arranged in hexagons, pentagons, or both. Most known fullerenes have 12 pentagons and varying numbers of hexagons depending on the size of the molecule. Common fullerenes include $C_{60}$ and $C_{70}$, although fullerenes comprising up to about 400 carbon atoms are also known.

$C_{60}$ has 30 carbon-carbon double bonds, and has been reported to readily react with oxygen radicals (Krusic et al., Science, 1991, 254:1183-1185). Other fullerenes have comparable numbers of carbon-carbon double bonds and would be expected to be similarly reactive with oxygen radicals. Native fullerenes are generally only soluble in apolar organic solvents, such as toluene or benzene. To render fullerenes water-soluble, as well as to impart other properties to fullerene-based molecules, a number of fullerene substituents have been developed.

Methods of substituting fullerenes with various substituents are known in the art. Methods include 1,3-dipolar additions (Sijbesma et al., J. Am. Chem. Soc. (1993) 115:6510-6512; Suzuki, J. Am. Chem. Soc. (1992) 114:7301-7302; Suzuki et al., Science (1991) 254:1186-1188; Prato et al., J. Org. Chem. (1993) 58:5578-5580; Vasella et al., Angew. Chem. Int. Ed. Engl. (1992) 31:1388-1390; Prato et al., J. Am. Chem. Soc. (1993) 115:1148-1150; Maggini et al., Tetrahedron Lett. (1994) 35:2985-2988; Maggini et al., J. Am. Chem. Soc. (1993) 115:9798-9799; and Meier et al., J. Am. Chem. Soc. (1994) 116:7044-7048), Diels-Alder reactions (Iyoda et al., J. Chem. Soc. Chem. Commun. (1994) 1929-1930; Belik et al., Angew. Chem. Int. Ed. Engl. (1993) 32:78-80; Bidell et al., J. Chem. Soc. Chem. Commun. (1994) 1641-1642; and Meidine et al., J. Chem. Soc. Chem. Commun. (1993) 1342-1344), other cycloaddition processes (Saunders et al., Tetrahedron Lett. (1994) 35:3869-3872; Tadeshita et al., J. Chem. Soc. Perkin. Trans. (1994) 1433-1437; Beer et al., Angew. Chem. Int. Ed. Engl. (1994) 33:1087-1088; Kusukawa et al., Organometallics (1994) 13:4186-4188; Averdung et al., Chem. Ber. (1994) 127:787-789; Akasaka et al., J. Am. Chem. Soc. (1994) 116:2627-2628; Wu et al., Tetrahedron Lett. (1994) 35:919-922; and Wilson, J. Org. Chem. (1993) 58:6548-6549); cyclopropanation by addition/elimination (Hirsch et al., Agnew. Chem. Int. Ed. Engl. (1994) 33:437-438 and Bestmann et al., C. Tetra. Lett. (1994) 35:9017-9020); and addition of carbanions/alkyl lithiums/Grignard reagents (Nagashima et al., J. Org. Chem. (1994) 59:1246-1248; Fagan et al., J. Am. Chem. Soc. (1994) 114:9697-9699; Hirsch et al., Agnew. Chem. Int. Ed. Engl. (1992) 31:766-768; and Komatsu et al., J. Org. Chem. (1994) 59:6101-6102); among others. The synthesis of substituted fullerenes is reviewed by Murphy et al., U.S. Pat. No. 6,162,926.

The discovery of the fullerenes in 1985, and the subsequent development of synthetic methods for the preparation of large-scale quantities of the allotropes of carbon has generated considerable interest and opened a whole new field of carbon chemistry.

Fullerenes are defined as closed-cage polyhedrons made up entirely of $sp^2$-hybridized carbon atoms that contain exactly 12 pentagonal faces (known as Euler's theorem) and (n/2-10) hexagonal faces where n is the number of carbon atoms (n must be even and greater than twenty). The soccer ball-shaped fullerene $C_{60}$ has the highest theoretically possible symmetry, icosahedral ($I_h$). It is the most abundant fullerene that is produced during the graphite combustion production of the materials, followed by $C_{70}$.

$C_{60}$ can be functionalized by well known methods of synthetic organic chemistry. The formation of $C_{60}$ derivatives (i.e., covalently modified $C_{60}$) nearly always involves the addition of a functional group (addend) across one or more of its 30 double bonds. When only one addend is attached, the fullerene derivative is termed a "monoadduct," with two, a "bisadduct," etc.

Another advantage of the spherical $C_{60}$ molecule for PDT is its large surface area of ~200 Å$^2$ compared to ≦100 Å$^2$ for other "flat" rigid PS, maximizing exposure to $O_2$. Additionally, the versatility of the $C_{60}$ scaffolding allows a tailoring of the hydrophobicity/hydrophilicity by simple synthetic methods, providing, as a nonlimiting example, any of a number of structures expected to be absorbed through the skin. Advantageously, $C_{60}$ and its derivatives are also thermally and photochemically stable (minimal photobleaching).

The present invention relates in one aspect to compositions comprising a functionalized (substituted, derivatized) fullerene comprising a fullerene core ($C_n$) where n is an even integer greater than or equal to 60, and at least one functional group bonded to at least one carbon atom of the fullerene core.

In one embodiment, the functionalized fullerene is a compound of the generic formula I:

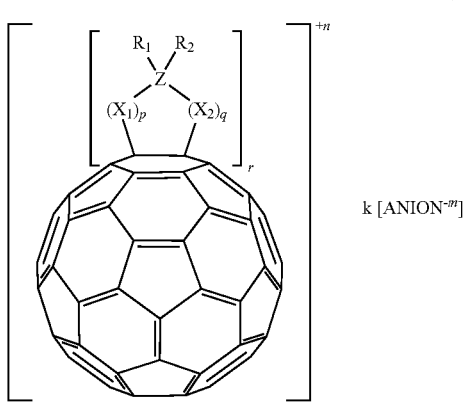

(Formula I)

k [ANION$^{-m}$]

wherein

Z is carbon, nitrogen or phosphorus;

$R_1$ and $R_2$ are independently selected from the group consisting of $C_1$-$C_{12}$alkyl, $C_2$-$C_{12}$alkenyl, $C_2$-$C_{12}$alkynyl, $C_3$-$C_8$cycloalkyl, (aryl)$C_0$-$C_4$alkyl, (heteroaryl)$C_0$-$C_4$alkyl, or a group of the formula C(O)—N($R_4$)($R_5$)($R_6$); or $ZR_1R_2$ taken in combination form a 3-20 member heterocyclic ring having 1-6 ring heteroatoms selected from nitrogen and phosphorus and having at least one quaternary ammonium cation or quaternary phosphonium cation;

$R_4$ and $R_5$ are independently selected from hydrogen or a group selected from $C_1$-$C_{12}$alkyl, $C_2$-$C_{12}$alkenyl, $C_2$-$C_{12}$alkynyl, $C_3$-$C_7$cycloalkyl, $C_3$-$C_8$ (aryl)$C_0$-$C_4$alkyl, and (heteroaryl)$C_0$-$C_4$alkyl each of which groups is substituted with 0-3 substituents selected from hydroxy, amino, mono-, di-, or tri-($C_1$-$C_4$alkyl)amino, halogen, quaternary ammonium cations, quaternary phosphonium cations;

$R_6$ is absent, hydrogen or a group selected from $C_1$-$C_{12}$alkyl, $C_2$-$C_{12}$alkenyl, $C_2$-$C_{12}$alkynyl, $C_3$-$C_7$cycloalkyl, $C_3$-$C_8$cycloalkyl, (aryl)$C_0$-$C_4$alkyl, and (heteroaryl)$C_0$-$C_4$alkyl each of which groups is substituted with 0-3 substituents selected from hydroxy, amino, mono-, di-, or tri-($C_1$-$C_4$alkyl)amino, halogen, quaternary ammonium cations, quaternary phosphonium cations;

$X_1$ and $X_2$ are independently selected at each occurrence from the group consisting of $CH_2$ and $CHR_3$, wherein $R_3$ is a $C_1$-$C_6$alkyl which is independently selected at each occurrence of $R_3$;

r is 1, 2, 3, or 4;

p and q are independently selected from 0, 1, 2, or 3 such that $0 \leq (p+q) \leq 4$;

ANION is at least one organic or inorganic anion;

m is a negative integer corresponding to the net negative charge of each ANION equivalent;

n is a positive integer corresponding to the net positive charge of the substituted buckminsterfullerene cation; and k is the quotient of n/m.

Certain other compounds of formula I include those compounds in which the C60-fullerene is substituted by a Cn-fullerene wherein n is an integer of between 50 and about 84.

Another embodiment is a compound according to formula I, wherein

Z is nitrogen or phosphorus;

$X_1$ and $X_2$ are methylene;

p=q=1;

$R_1$ and $R_2$ are independently selected $C_1$-$C_6$alkyl, (aryl)$C_0$-$C_1$alkyl, or (heteroaryl)$C_0$-$C_1$alkyl;

r is 2, 3, or 4; and n≥r.

Another embodiment is a compound according to formula I, referred to herein as compounds of formula II, wherein Z is nitrogen or phosphorus;

$X_1$ and $X_2$ are methylene;

p=q=1;

$R_1$ is $C_1$-$C_6$alkyl, (aryl)$C_0$-$C_1$alkyl, or (heteroaryl)$C_0$-$C_1$alkyl;

$R_2$ is (aryl)$C_0$-$C_1$alkyl, or (heteroaryl)$C_0$-$C_1$alkyl;

r is 1, 2, 3, or 4; and n≥r.

Another embodiment is a compound according to formula II, wherein

Z is nitrogen;

$X_1$ and $X_2$ are methylene;

p=q=1;

$R_1$ and $R_2$ are independently selected from methyl, ethyl, propyl or isopropyl;

r is 2, 3, or 4; and n≥r

Another embodiment is the compound according to formula I, wherein

Z is carbon;

p=q=0;

$R_1$ and $R_2$ are independently selected groups of the formula C(O)—N($R_4$)($R_5$)($R_6$); or $ZR_1R_2$ taken in combination form a 6-20 member heterocyclic ring having 1-6 ring heteroatoms selected from nitrogen and phosphorus and having at least one quaternary ammonium cation or quaternary phosphonium cation;

$R_4$ and $R_5$ are independently selected from hydrogen or a group selected from $C_1$-$C_{12}$alkyl, $C_2$-$C_{12}$alkenyl, $C_2$-$C_{12}$alkynyl, $C_3$-$C_7$cycloalkyl, $C_3$-$C_8$ (aryl)$C_0$-$C_4$alkyl, and (heteroaryl)$C_0$-$C_4$alkyl each of which groups is substituted with 0-3 substituents selected from hydroxy, amino, di-, or tri-($C_1$-$C_2$alkyl)amino, halogen, quaternary ammonium cations, quaternary phosphonium cations; and $R_6$ is absent, hydrogen or a group selected from $C_1$-$C_{12}$alkyl, $C_2$-$C_{12}$alkenyl, $C_2$-$C_{12}$alkynyl, $C_3$-$C_7$cycloalkyl, $C_3$-$C_8$cycloalkyl, (aryl)$C_0$-$C_4$alkyl, and (heteroaryl)$C_0$-$C_4$alkyl each of which groups is substituted with 0-3 substituents selected from hydroxy, amino, mono-, di-, or tri-($C_1$-$C_2$alkyl)amino, halogen, quaternary ammonium cations, quaternary phosphonium cations.

Another embodiment is a compound according to formula II, referred to herein as formula III, wherein $R_1$ and $R_2$ are independently selected groups of the formula C(O)—N($R_4$)($R_5$)($R_6$);

$R_4$ is $C_2$-$C_6$alkyl substituted with 1-3 substitutents selected from hydroxy, amino, di-, or tri-($C_1$-$C_2$alkyl)amino, and quaternary ammonium cations;

$R_5$ is hydrogen, $C_1$-$C_6$alkyl substituted with 0-3 substitutents selected from hydroxy, amino, and quaternary ammonium cations; and $R_6$ is absent, hydrogen, or $C_1$-$C_6$alkyl substituted with 0-3 substitutents selected from hydroxy, amino, di-, or tri-($C_1$-$C_2$alkyl)amino, and quaternary ammonium cations.

Another embodiment is a compound according to formula III, referred to herein as formula IV, wherein
wherein $R_1$ and $R_2$ are the same and are selected from the group consisting of:

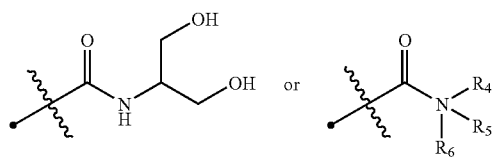

wherein $R_4$ is methyl, ethyl or propyl or isopropyl;

$R_5$ and $R_6$ are independently selected from methyl, ethyl, 2-(N,N-dimethylamino)ethyl, 3-(N,N-dimethylamino)propyl, 2-(N,N,N-trimethylammonium)ethyl, or 3-(N,N,N-trimethylammonium)propyl.

Another embodiment is a compound according to formula IV, wherein r is 1.

Another embodiment is a compound according to formula IV, wherein r is 2.

Another embodiment is a compound according to formula IV, wherein r is 3.

Another embodiment is a compound according to formula I, wherein p=q=0; and $ZR_1R_2$, taken in combination, form a 7-20 member heterocyclic ring having 2 to 6 nitrogen atoms wherein at least one of the nitrogen atoms is a quaternary ammonium cation. (Formula V).

Another embodiment is a compound according to formula V, referred to herein as formula VI wherein $ZR_1R_2$ is a heterocyclic ring of the formula:

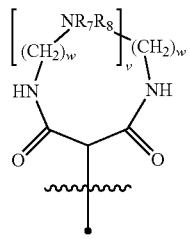

wherein w is independently selected at each occurrence from 1, 2 or 3;

v is 0, 1, 2, or 3;

$R_7$ is independently selected at each occurrence from hydrogen, $C_1$-$C_6$alkyl substituted with 0-3 substitutents selected from hydroxy, amino, and quaternary ammonium cations; and $R_8$ is independently selected at each occurrence from absent, hydrogen, or $C_1$-$C_6$alkyl substituted with 0-3 substitutents selected from hydroxy, amino, di-, or tri-($C_1$-$C_2$alkyl) amino, and quaternary ammonium cations; and wherein at least one $NR_7R_8$ is a quaternary ammonium cation or is substituted by a quaternary ammonium cation.

Another embodiment is a compound according to formula VI, wherein v is 1, 2 or 3;

w is 2;

$R_7$ is independently selected from the group of methyl, ethyl or propyl or isopropyl;

$R_8$ are independently selected from methyl, ethyl, 2-(N,N-dimethylamino)ethyl, 3-(N,N-dimethylamino)propyl, 2-(N,N,N-trimethylammonium)ethyl, or 3-(N,N,N-trimethylammonium)propyl.

The chemical structures of certain preferred embodiments of the fullerene-based photosensitizer compounds of the invention are shown in Table 2.

TABLE 1

Chemical structures of the fullerene derivatives.

NI = non-ionic, CI = cationic, N = nitrogenous base.

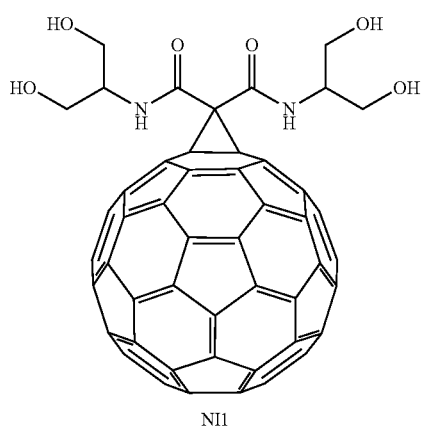

NI1

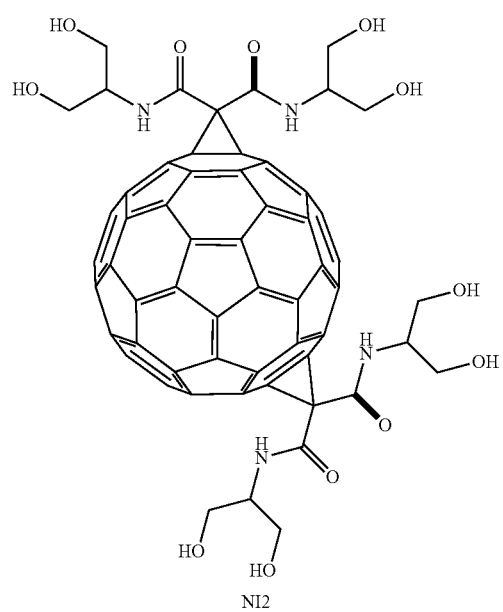

NI2

TABLE 1-continued

Chemical structures of the fullerene derivatives.
NI = non-ionic, CI = cationic, N = nitrogenous base.

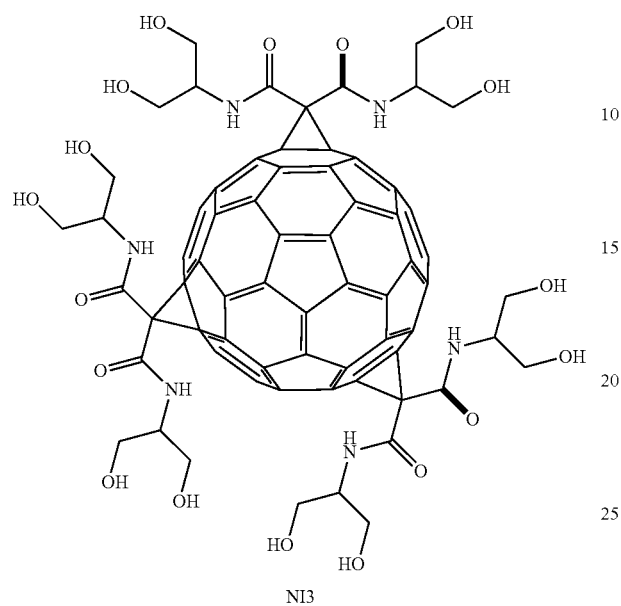

NI3

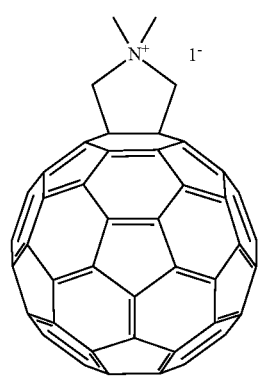

CI1

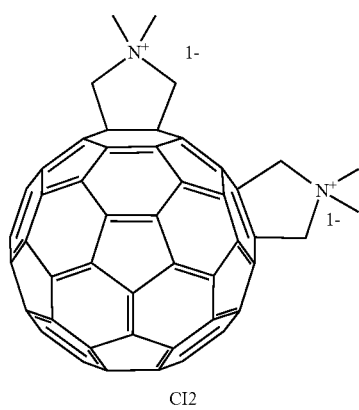

CI2

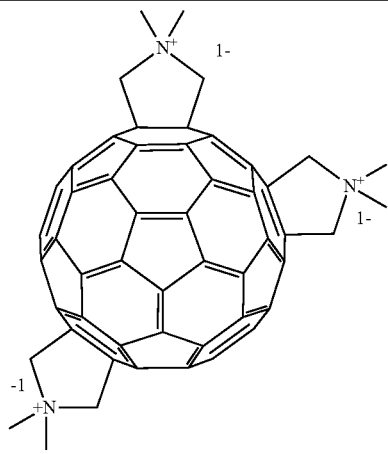

CI3

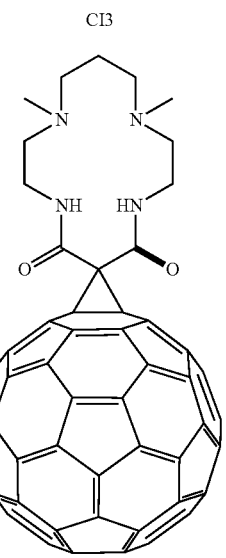

N1

Synthetic schemes for particular functionalized fullerene PS are further described in Examples 1-4, infra.

A pharmaceutical composition in accordance with the invention can contain a suitable concentration of an active agent (i.e., a functionalized fullerene compound) and may also comprise certain other components. For example, in some embodiments, pharmaceutical compositions of the present invention are formulated with pharmaceutically acceptable carriers or excipients, such as water, saline, aqueous dextrose, glycerol, or ethanol, and may also contain auxiliary substances such as wetting or emulsifying agents, and pH buffering agents in addition to the active agent.

The pharmaceutical composition can also comprise, or can be applied in combination with, an optical clearing agent to enhance the photoactive effectiveness of the funcionalized fullerene compound by allowing more effective penetration of light through tissue. At visible and near infrared wavelengths, optical scattering dominates over absorption and is much more significant in reducing light penetration into biological tissues. Optical clearing is a method for inducing a transient reduction in optical scattering by biological tissue. Studies have demonstrated increased light penetration depth using hyperosmotically active chemical agents such as glycerol, propylene glycol, ethylene glycol, DMSO, glucose or dextrose, oleic acid, linoleic acid, etc., which are applied to the skin or tissue. Various mechanisms for optical clearing have been proposed. Although the mechanism of optical clearing is still not entirely understood, it has been inferred that hyperosmotic agents reduce random scattering primarily by better refractive index matching, dehydration, and collagen dissociation.

One or more optical clearing agents can be applied to tissue simultaneously with the pharmaceutical composition, as a combined formulation. Alternatively, one or more optical clearing agents can be applied some time prior to the application of the pharmaceutical composition, as a separate formulation. One or more optical clearing agents can be applied to tissue simultaneously with the application of light or can be applied some time prior to the application of light.

The pharmaceutical composition can further comprise or be used in combination with a permeation enhancer (also termed an "absorption enhancer"), which promotes the distribution and penetration of the functionalized fullerene compound in the tissue being treated by PDT. Examples include but are not limited to: DMSO, polyethylene glycol, non-ionic surfactants, ionic surfactants, vitamin A, and steroids.

Kits

The invention also includes kits for killing microbes and/or treating microbial infections in a subject comprising a functionalized fullerene compound and instructions for using the functionalized fullerene compound to kill the microbe or to treat the infection in accordance with the methods described herein.

The kits of the invention have many applications. For example, the kits can be used to provide reagents and therapeutics for killing microbes in a subject or associated with inanimate objects. The kits of the invention include instructions for the reagents, equipment (test tubes, reaction vessels, needles, syringes, etc.), standards for calibrating the administration, and/or equipment provided or used to conduct the treatment. The standard or control information can be compared to a test sample to determine, for example, if the dosage is correct.

III. Methods of the Invention

Photodynamic therapy according to the present invention may be utilized in the eradication of microcellular organisms, such as bacteria, acellular organisms, and cells infected with microcellular and acellular organisms. Acellular organisms are defined broadly to include organisms not composed of cells, e.g., bodies of protoplasm made discrete by an enveloping membrane (also referred to as a capsule, envelope, or capsid). Examples of acellular organisms include, but are not limited to, viruses, spores, fungi, and other virus-like agents such as viroids, plasmids, prions, and virinos, and other infectious particles. Acellular and microcellular organisms are collectively referred to herein as microbes.

Structures of cellular and acellular organisms are described as follows. Procaryotic cells are cellular organisms, including bacteria. The component structures of procaryotic cells include appendages, cell envelope, and protoplasm. The cell envelope further includes the glycocalyx (capsules, slime layers), cell wall, and cell membrane. All bacterial cells invariably have a cell envelope, glycocalyx, cell membrane, ribosomes, and a nucleoid; the majority have a cell wall. Although they are common to many species, flagella, pili, fimbriae, capsules, slime layers, and granules are not universal components of all bacteria. Organisms of the genera *Chlamydia*, *Rickettsia*, and *Ehrlichea*, referred to as obligate intracellular bacteria, are prokaryotes that differ from most other bacteria with respect to their very small size and obligate intracellular parasitism.

Eucaryotic cells are typical of certain microbial groups (fungi, algae, protozoans, and helminth worms), as well as all animal and plants. Eucaryotic cells have component structures including appendages, surface structures, cytoplasmic membrane, nucleus, cytoplasm, cytoskeleton, and ribosomes. The surface structures may include glycocalyx, capsules, and slimes.

Virus particles are not cells and they neither possess procaryotic nor eucaryotic structural qualities. Instead, they are large, complex macromolecules, with parts made up of repeating molecular subunits. Virus particles include component structures of a covering and a central core. The covering includes a capsid and in some viruses, an envelope. All viruses have a protein capsid or shell that surrounds the nucleic acid strand. Members of 12 of the 17 families of animal viruses possess an additional covering external to the capsid called an envelope, which is actually a modified piece of the hosts cell membrane. Viruses that lack this envelope are considered naked nucleocapsids. Special virus-like infectious agents include the prion (proteinacious infectious particles) and viroids.

Photodynamic compositions of the present invention can be utilized in the eradication of microcellular organisms, acellular organisms, and cells infected with microcellular and acellular organisms. Particularly preferred photodynamic compositions are based on functionalized fullerenes as discussed in further detail infra. Photodynamic compositions of the invention may be provided in a liquid, gaseous, or solid form, including but not limited to liquids, solutions, topical ointments, or powders.

In one embodiment, the present invention is directed to a method for providing antimicrobial therapy, comprising:

administering to a subject in need thereof an effective amount of a composition comprising a functionalized fullerene compound, wherein the functionalized fullerene compound is any one of the compounds as described above;

directing light onto the administered functionalized fullerene compound to produce a cytotoxic species; and killing microbial cells associated with or proximal to the functionalized fullerene compound, thereby providing antimicrobial therapy.

In another embodiment, the present invention is directed to a method for killing a microbe, comprising:

providing a composition comprising a functionalized fullerene compound, wherein the functionalized fullerene is any one of the compounds as described above;

directing light onto the functionalized fullerene compound to produce a cytotoxic species; and killing the microbe associated with or proximal to the functionalized fullerene compound by reaction with the cytotoxic species. Methods of the invention permit but do not require direct contact with the microbe of interest. Typically, production of a cytotoxic species proximal to the microbe is sufficient to kill the microbe.

Administration

An "effective amount" of a functionalized fullerene compound is an amount sufficient to effect a beneficial or desired clinical result (e.g., a photodynamic effect). An effective amount can be administered in one or more doses. In terms of treatment, an effective amount is an amount that is sufficient to palliate, ameliorate, stabilize, reverse or slow the progression of a condition caused by infection. The effective amount is generally determined by the physician on a case-by-case basis and is within the skill of one in the art. In accordance with certain preferred aspects of the invention, "an effective amount of a functionalized fullerene compound" of the invention is defined as an amount sufficient to yield an acceptable antimicrobial effect, i.e., to kill pathogens such as bacteria, yeast, fungus etc. with minimal adverse effect on the cells of the mammalian subject of the PDT treatment.

As a rule, the dosage for in vivo therapeutics will vary. Several factors are typically taken into account when determining an appropriate dosage. These factors include age, sex and weight of the patient, the condition being treated, and the severity of the condition.

Suitable dosages and formulations of functionalized fullerene compound can be empirically determined by the administering physician. Standard texts, such as Remington: The Science and Practice of Pharmacy, 17th edition, Mack Publishing Company, and the Physician's Desk Reference, each of which is incorporated herein by reference, can be consulted to prepare suitable compositions and doses for administration. A determination of the appropriate dosage is within the skill of one in the art given the parameters for use described herein.

Administration can be in any order. Typically the functionalized fullerene compound is administered, followed by application of light. A light source is utilized to practice embodiments of the present invention. The light source may be laser light source, a high intensity flash lamp, a light-emitting diode (LED) or other illumination source as appreciated by those skilled in the relevant arts. A broad-spectrum light source may be utilized; however a narrow spectrum light source is one preferred light source. The light source may be selected with reference to the specific photosensitive material, as photosensitive materials may have an associated range of photoactivation. In some instances a laser light source may be used to practice the present invention. A variety of laser light sources is currently available, and the selection of a particular laser light source for implementing the PDT would readily be appreciated by those skilled in the relevant arts. A laser source may be selected with regard to the choice of wavelength, beam diameter, exposure time and sensitivity of the cellular and/or acellular organisms.

In preferred embodiments, the light source is utilized for a period of time necessary to effect a photodynamic response. The period of time for photodynamic activation of the photosensitive material is preferably between 5 seconds and 1 hour. Even more preferably, the period of time for light illumination is between 2 and 20 minutes.

A variety of light delivery devices may be utilized to practice the present invention. A hand manipulable light wand or fiber optic device may be used to illuminate tissue within a living body. Such fiber optic devices may include a disposable fiber optic guide provided in kit form with a solution containing a photosensitive material. Other potential light devices for use in accordance with the present invention include the devices disclosed in U.S. Pat. No. 6,159,236, entitled Expandable treatment device for photodynamic therapy and method of using same, and U.S. Pat. No. 6,048,359, entitled Spatial orientation and light sources and method of using same for medical diagnosis and photodynamic therapy, both incorporated by reference in their entireties herein.

Repeat administrations of a treatment protocol may also be necessary or desired, including repeat administrations of photosensitive functionalized fullerenes and light activation. The repeat administrations may include different photosensitive materials and/or different compounds than earlier administered. Repeat administrations of the treatment protocol may continue for a period of time.

In general, an effective amount of a functionalized fullerene compound will be in the range of from about 0.1 to about 10 mg by injection or from about 5 to about 100 mg orally. Such dosages may vary, for example, depending on whether multiple administrations are given, tissue type and route of administration, the condition of the individual, the desired objective and other factors known to those of skill in the art.

Compositions of the present invention are administered by a mode appropriate for the form of composition. Available routes of administration include subcutaneous, intramuscular, intraperitoneal, intradermal, oral, intranasal, intrapulmonary (i.e., by aerosol), intravenously, intramuscularly, subcutaneously, intracavity, intrathecally or transdermally, alone or in combination with other pharmaceutical agents. Therapeutic compositions of photosensitizers are often administered by injection or by gradual perfusion, or by topical application to the skin or mucous membrane in need of treatment.

Compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or liquid aerosol when used with an appropriate aerosolizer device. Although not required, compositions are preferably supplied in unit dosage form suitable for administration of a precise amount. Also contemplated by this invention are slow-release or sustained release forms, whereby a relatively consistent level of the active compound are provided over an extended period.

Another method of administration is intravascular, for instance by direct injection into the blood vessels of the infected tissue or surrounding area.

Further, it may be desirable to administer the compositions locally to the area in need of treatment. This can be achieved, for example, by local infusion during surgery, by injection, by means of a catheter, or by means of an implant, said implant being of a porous, non-porous, or gelatinous material, including membranes, such as silastic membranes, or fibers. A suitable such membrane is Gliadel® provided by Guilford Pharmaceuticals Inc.

In alternative embodiments, photodynamic compositions of the invention can be used to sterilize inanimate objects which harbor microbes, such as surfaces, liquids (e.g., bood products, bodily fluids), surgical equipment, textile products and the like.

Microbial Infections and Associated Disorders

Infectious diseases and conditions affect a wide range of tissues of one or more organs or organ systems of the body including, but are not limited to, the peripheral nervous system, hematological system, bone marrow, the central nervous system, skin, appendix, gastrointestinal tract (including but not limited to esophagus, duodenum, and colon), respiratory/pulmonary system (including but not limited to lung, nose, pharynx, larynx), eye, genito-reproductive system, gums, liver/biliary ductal system, renal system (including but not limited to kidneys, urinary tract, bladder), connective tissue (including but not limited to joints, cartilage), cardiovascular system, muscle, heart, spleen, breast, lymphatic system, ear, endocrine/exocrine system (including but not limited to lacrimal glands, salivary glands, thyroid gland, pancreas), and bone/skeletal system.

Both gram negative and gram positive bacteria can be killed by the methods of the invention. Such gram positive bacteria include, but are not limited to, *Pasteurella* species, Staphylococci species, and Streptococcus species, including S. aureus. Gram negative bacteria include, but are not limited to, Escherichia coli, Pseudomonas species, and Salmonella species.

Specific examples of infectious bacteria susceptible to killing by the PDT methods and compositions of the invention include but are not limited to: Helicobacter pyloris, Borelia burgdorferi, Legionella pneumophilia, Mycobacteria sps (e.g. M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes (Group A Streptococcus), Streptococcus agalactiae (Group B Streptococcus), Streptococcus (viridans group), Streptococcus faecalis, Streptococcus bovis, Streptococcus (anaerobic sps.), Streptococcus pneumoniae, pathogenic Campylobacter sp., Enterococcus sp., Haemophilus influenzae, Bacillus antracis, corynebacterium diphtheriae, corynebacterium sp., Erysipelothrix rhusiopathiae, Clostridium perfringers, Clostridium tetani, Enterobacter aerogenes, Klebsiella pneumoniae, Pasturella multocida, Bacteroides sp., Fusobacterium nucleatum, Streptobacillus moniliformis, Treponema pallidium, Treponema pertenue, Leptospira, Rickettsia, and Actinomyces israelli.

Fungi can also be killed by antimicrobial PDT in accordance with the invention. Examples of fungi include Cryptococcus neoformans, Histoplasma capsulatum, Coccidioides immitis, Blastomyces dermatitidis, Chlamydia trachomatis, and Candida albicans.

Other infectious organisms that can be targeted (e.g., protists) include Plasmodium spp. such as Plasmodium falciparum, Plasmodium malariae, Plasmodium ovale, and Plasmodium vivax and Toxoplasma gondii. Blood-borne and/or tissues parasites include Plasmodium spp., Babesia microti, Babesia divergens, Leishmania tropica, Leishmania spp., Leishmania braziliensis, Leishmania donovani, Trypanosoma gambiense and Trypanosoma rhodesiense (African sleeping sickness), Trypanosoma cruzi (Chagas' disease), and Toxoplasma gondii.

Other medically relevant microorganisms have been described extensively in the literature, e.g., see C. G. A Thomas, Medical Microbiology, Bailliere Tindall, Great Britain 1983, the entire contents of which is hereby incorporated by reference.

The invention will be more fully understood by reference to the following examples. These examples, however, are merely intended to illustrate the embodiments of the invention and are not to be construed to limit the scope of the invention.

EXAMPLES

Example 1

Synthesis of Nonionic Fullerene Derivatives

This Example describes the synthesis of a series of functionalized nonionic $C_{60}$ fullerene derivatives with one, two, or three polar diserinol groups (e.g., NI1, NI2, NI3, as shown in Table 2, supra).

This synthesis was carried out as described below and shown in Scheme 1.

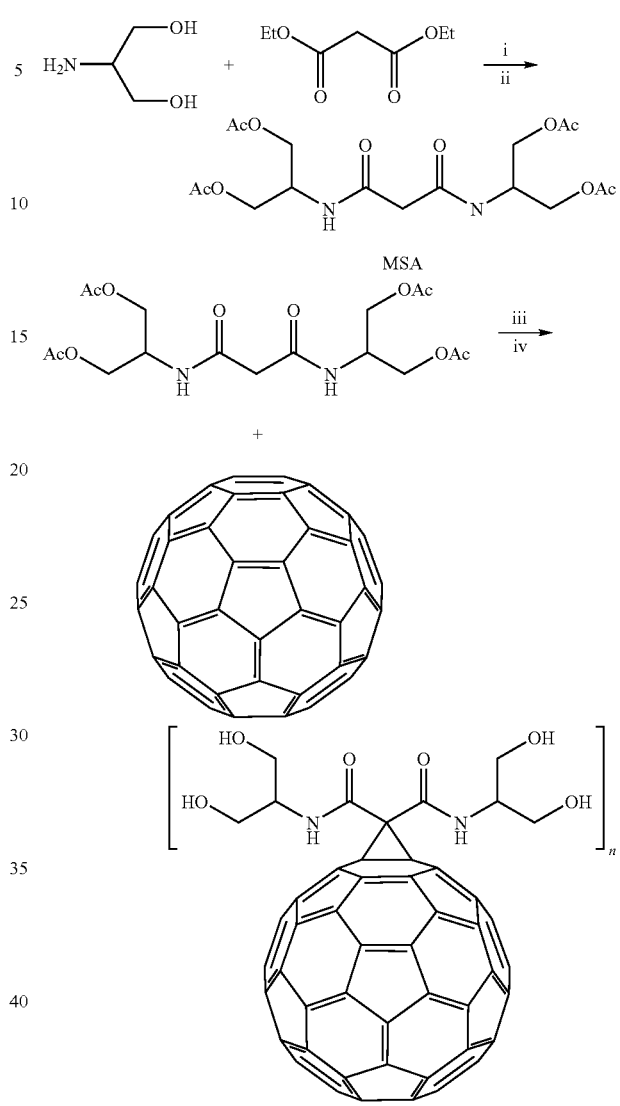

Serinol (2.05 equivalents) and diethylmalonate (1 equivalent) were reacted at 200° C. for 45 minutes in an open tube. Then acetic anhydride (4.1 equivalents) and pyridine (4.1 equivalents) were added and stirred for 18 hours at room temperature. The product termed MSA thus obtained was recrystallized using a mixture of hexane and ethyl acetate.

Purified $C_{60}$ (200 mg, 0.28 mmol) was dissolved in toluene (250 ml) by sonicating for 10 minutes and nitrogen was purged for 30 minutes. Then $CB_4$ (46.1 mg, 0.14 mmol) as a solid directly, MSA (58.2 mg. 0.14 mmol) in acetone (3 ml), and 1,8-Diazabicyclo[5.4.0]undec-7-ene (31.7 mg, 0.21 mmol) in toluene (5 ml) were added. The reaction mixture as stirred at room temperature for 4.5 hours under nitrogen atmosphere. Solvents were removed on a rotavap under vacuum. The product was dissolved in a minimum amount of chloroform and loaded onto a silica gel column (1 in×9 in) and eluted with dichloromethane containing 0-2% methanol to collect pure N11, N12 and N13. The compounds were characterized by matrix assisted laser desorption ionization mass spectrometry (MALDI-MS) as follows: N11—calculated mass 1137.02 and observed mass 1137.56; N12—calculated mass 1553.40 and observed mass 1153.77; N13—calculated mass 1969.78 and observed mass 1970.26.

NMR data were obtained for $C_{60}$(MSA)-protected NI1: $^1$H NMR (400 MHz, $CDCl_3$, TMS ref.) δ (ppm) 2.10 (s, 12H, $CH_3$), 4.34-4.41 (m, 8H, $CH_2$), 4.68-4.72 (m, 2H, CH), 7.37 (br d, J 56.4 Hz, 2H, NH).

Deprotection of —OH groups was achieved by treating NI1-3 with an excess of potassium carbonate in methanol and deionized water at room temperature for 90 minutes. Potassium ions were removed by adding strong cation exchange resin (Biorad AG MP-50W, treated with 1M HCl) to the reaction mixture until the pH reached 7. The solution was filtered and solvents were removed on a rotavap to obtain pure NI1, NI2, and NI3.

Example 2

Synthesis of Cationic Fullerene Derivatives

This Example describes a scheme for synthesis of cationic fullerene derivatives (e.g., CI1, CI2, and CI3, as illustrated in Table 2, supra).

The synthesis of compounds CI1-3 was carried out using published procedures (Wharton, T., Kini, V. U., Mortis, R. A., and Wilson, L. J. (2001). New non-ionic, highly water-soluble derivatives of C60 designed for biological compatibility. *Tetrahedron Lett.* 42, 5159-5162, Wharton, T., and Wilson, L. J. (2002). Highly-iodinated fullerene as a contrast agent for X-ray imaging. *Bioorg. Med. Chem.* 10, 3545-3554, Maggini, M., Scorrano, G., and Prato, M. (1993). Addition of azomethine ylides to C60: synthesis, characterization, and functionalization of fullerene pyrrolidines. *J. Am. Chem. Soc.* 115, 9798-9799 and Cassell, A. M., Scrivens, W. A., and Tour, J. M. (1998). Assembly of DNA/fullerene hybrid materials. *Angew. Chem. Int. Ed. Engl.* 37, 1528-1530) with modifications as described below, and illustrated in Scheme 2.

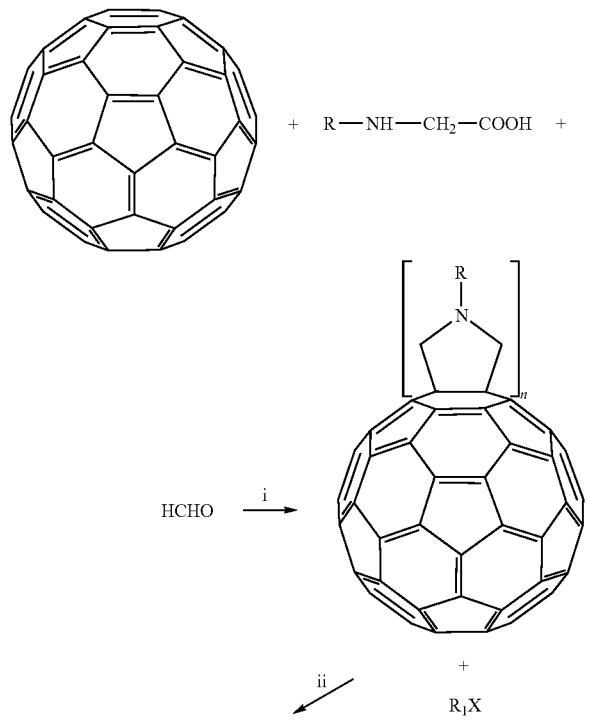

Scheme 2. Synthesis of CI1, CI2, CI3.

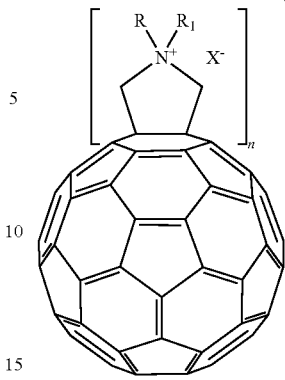

Purified $C_{60}$ (200 mg, 0.28 mmol) was dissolved in toluene (260 ml) by sonicating for 5 minutes. To this solution were added sarcosine (50.8 mg, 0.57 mmol) and paraformaldehyde (40.9 mg, 1.36 mmol) for CI1; sarcosine (63.5 mg, 0.71 mmol) and paraformaldehyde (35.79 mg, 1.19 mmol) for CI2; or sarcosine (88.9 mg, 1.0 mmol) and paraformaldehyde (46.0 mg, 1.53 mmol) for CI3, as solids directly. The reaction mixture was refluxed for 2 hours for CI1; overnight for CI2; and 3 hours for CI3. Solvents were removed on a rotavap under vacuum.

The product was dissolved in a minimum amount of toluene and loaded onto a silica gel column (1 in×9 in) packed with toluene and eluted with toluene containing 0-5% acetone to collect pure CI1, CI2, or CI3, with yields of 30-40% purity. The purity of the compounds in terms of nono-, bis-, and tris-substitutions was confirmed by thin layer chromotography (TLC).

Methylation of CI1, CI2, or CI3 was carried out by dissolving the compounds in a large excess of methyl iodide (1 ml per 20 mg CI1-3) and stirring for 48-72 hours at room temperature (or 7 days in the case of CI3). Pure methylated products CI1, CI2, or CI3 were precipitated by adding hexanes, and the precipitates were collected, washed with toluene and dichloromethane, and dried. The compounds were characterized by electrospray mass spectrometry (ES-MS) as follows: CI1— calculated mass 792.08 and observed mass 792.04; CI2— calculated mass 864.16 and observed mass 432.05 ($M^{2+}$); and CI3— calculated mass 936.24 and observed mass 312.08 ($M^{3+}$).

NMR data were obtained for CI1 as follows: $^1$H NMR (400 MHz, 2:3 $CDCl_3$: DMSO-$d_6$, TMS ref.) δ (ppm) 4.08 (s, 6H, $CH_3$), 5.72 (s, 4H, $CH_2$). Referring to FIG. 1, UV-visible absorption spectra of the compounds were recorded in 1:9 DMSO:water at a concentration of 10 mM. More particularly, FIG. 1 shows UV-Visible absorption spectra of CI1-3 and toluidine blue O (TBO) at 10 μM concentration in 1:9 DMSO: water.

Example 3

Synthesis of Nitrogenous Fullerene Derivatives

This Example describes a scheme for synthesis of nitrogenous fullerene derivatives (e.g., N1 as illustrated in Table 2, supra).

The synthesis of compound N1 was carried out as described below and illustrated in Scheme 3.

Scheme 3. Synthesis of N1.

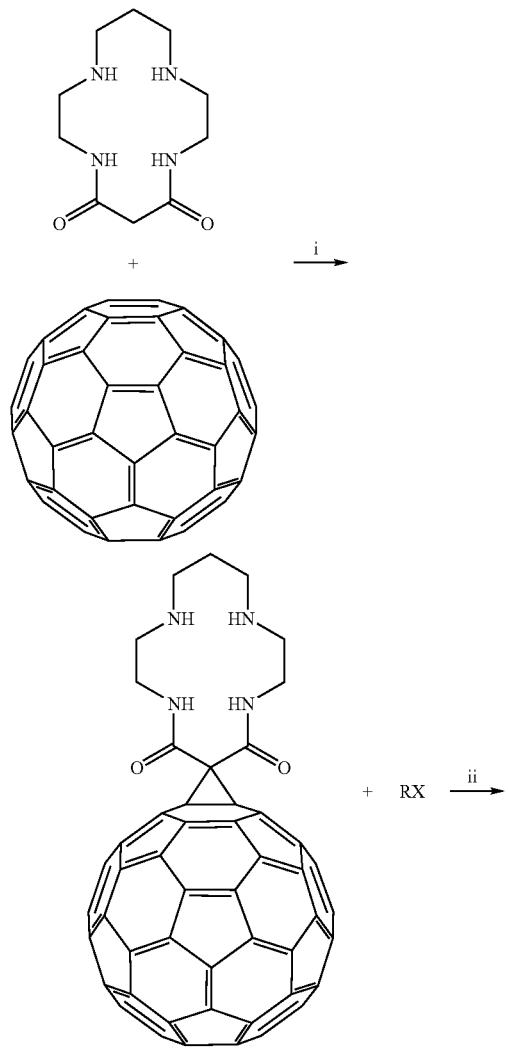

Purified $C_{60}$ (360 mg, 0.5 mmol) was dissolved in toluene (180 ml) by sonicating for 30 minutes and nitrogen was purged for 15 minutes. Then $CBr_4$ (83 mg, 0.25 mmol) as solid directly, 1,4,8,11-tetraazacyclotetradecane-5,7-dione (57 mg, 0.25 mmol) in methanol (1 ml) and toluene (9 ml), and DBU (57 mg, 0.375 mmol) in toluene (10 ml) were added. The reaction mixture was stirred at room temperature for 24 hours under nitrogen atmosphere. The product N1 was precipitated and filtered, washed with toluene and dried.

Methylation of N1 was carried out by suspending in a large excess of methyl iodide and stirring for 72 hours at room temperature. The methylated product N1 was precipitated and which was collected and washed with toluene and dichloromethane, and dried.

Example 4

Synthesis of Cationic CI4 and CI5 Fullerene Derivatives

The synthesis of cationic compounds CI4 and CI5 was carried out as described below, and illustrated in Scheme 4.

Scheme 4. Synthesis of CI4 and CI5.

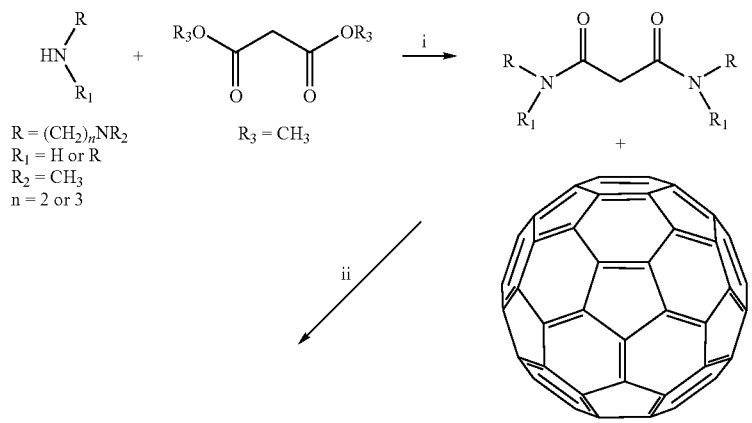

-continued

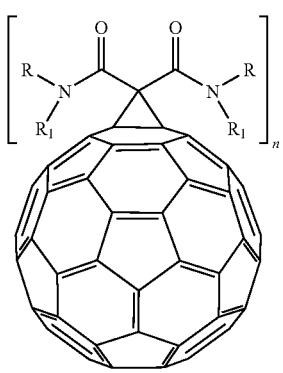
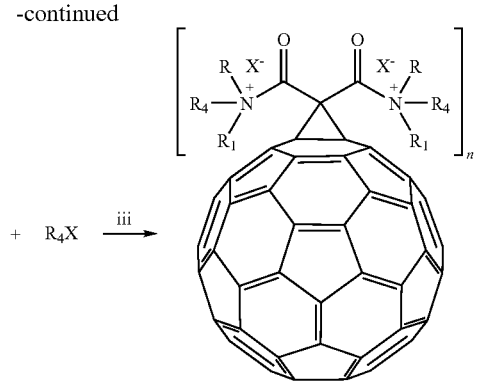

For synthesis of diquat-21, $(CH_3)_2N(CH_2)_2NH_2$ (2.05 equivalents) and dimethylmalonate (1 equivalent) were dissolved in toluene and reacted at 100° C. for 2 hours. The solvents were removed on a rotavap and added hexanes. The product was cooled in a refrigerator overnight and filtered. The product obtained as a pink waxy solid.

For synthesis of diquat-31, $(CH_3)_2N(CH_2)_2NH_2$ (2.05 equivalents) and dimethylmalonate (1 equivalent) were reacted at 120° C. for 2 hours. The solvents were removed on a rotavap. The product was obtained as a high viscous pale yellow liquid after vacuum drying for 60 hours at 20° C.

For synthesis of CI4 and CI5, purified $C_{60}$ (360 mg, 0.5 mmol) was dissolved in toluene (180 ml) by sonicating for 15 minutes and nitrogen was purged for 15 minutes. Then $CBr_4$ (83 mg, 0.25 mmol) as a solid directly, diquat (0.25 mmol) in toluene (5 ml), toluene (9 ml), and DBU (57 mg, 0.375 mmol) in toluene (10 ml) were added. The reaction mixture was stirred at room temperature for 4 hours under nitrogen atmosphere. The product $C_{60}$-diquat was precipitated and filtered, washed with toluene, and dried.

Methylation of $C_{60}$-diquat was carried out by dissolving the compounds in a large excess of methyl iodide and stirring for 72 hours at room temperature. The methylated product was precipitated and collected, washed with toluene and dichloromethane, and dried. The compounds were characterized by electrospray mass spectrometry (ES-MS) as follows. CI4—calculated mass 993.03 and observed mass 496.09 ($M^{2+}$); CI5—calculated mass 1021.08 and observed mass 510.11 ($M^{2+}$).

Example 5

Absorption Spectra of Derivatized Fullerenes

This Example describes one aspect of the characterization (determination of absorption spectra) of functionalized fullerenes NI1-3 and CI1-3 of the invention.

Functionalized fullerenes NI1-3 and CI1-3 were prepared as described above. There are eight possible regioisomers of the bis-substituted fullerenes and 46 possible regioisomers of the tris-substituted fullerenes. It was not practical to separate these mixtures of regioisomers into individual pure compounds; therefore, NI2 and NI3, and CI2 and CI3 were studied as mixtures of regioisomers. The identity of the compounds, however, was confirmed by mass spectrometry, giving molecular ions identical to those calculated. The proton and C13 NMR spectra of the immediate precursors of BF1 and BF4 have been reported (Wharton, T., Kini, V. U., Mortis, R. A., and Wilson, L. J. (2001). New non-ionic, highly water-soluble derivatives of C60 designed for biological compatibility. Tetrahedron Lett. 42, 5159-5162, Maggini, M., Scorrano, G., and Prato, M. (1993). Addition of azomethine ylides to C60: synthesis, characterization, and functionalization of fullerene pyrrolidines. J. Am. Chem. Soc. 115, 9798-9799).

The absorption spectra of CI1-3 and TBO, all at the same concentration of 10 µM in DMSO:water (i.e., 1:9), are shown in FIG. 1. The overall extinction coefficients of the fullerenes were in the following order: CI1>CI2>CI3. The shoulder in the UVA range moved from 340 nm for CI1 to 310 nm for CI2 and disappeared altogether for CI3 (FIG. 1).

Example 6

Distribution Coefficients of Derivatized Fullerenes

This Example describes studies performed to determine the distribution coefficients of fullerenes NI1-3 and CI1-3 of the invention.

Each compound was dissolved in a minimum amount of DMSO: CI1 (0.9 mg in 200 µl), CI2 (5.3 mg in 200 µl), CI3 (5.4 mg in 200 µl). Ten ml of DI water and 10 ml of 1-octanol were added in each compound and vigorously shaken for 2 min. and the vials of the compounds were settled down overnight. The phases were separated and UV-spectra of each phase were analyzed. Distribution coefficient of each compound was determined using absorbance of aqueous phases and organic phases at 330 nm.

The results of these determinations are presented in Table 2. Referring to Table 2, it will be appreciated that the hydrophilic character of fullerene derivatives increases with increasing number of cationic functional groups, whereas hydrophilicity decreases with increasing number of serinol groups.

TABLE 2

Octanol-water partition constants ($K_{ow}$) of Fullerene Derivatives NI1-3 and CI1-3.

| Compound | NI1 | NI2 | NI3 | CI1 | CI2 | CI3 |
|---|---|---|---|---|---|---|
| $K_{ow}$ | 0.025 | 0.032 | 0.078 | 140.80 | 1.28 | 0.37 |
| $LogK_{ow}$ | −1.61 | −1.49 | −1.11 | 2.15 | 0.11 | −0.43 |

Example 7

Determining Antimicrobial Properties of Derivatized Fullerenes

This Example describes exemplary materials and methods useful for testing antimicrobial activity of derivatized fullerenes prepared in accordance with the invention.

1. Microbial Strains and Culture Conditions

*Staphylococcus aureus* (ATCC #35556), *Escherichia coli* (ATCC #25922), and *Pseudomonas aeruginosa* (ATCC #BAA-47; PAO1) were cultured in brain-heart infusion (BHI) broth (Difco, BD Diagnosttic Systems, Sparks, Md.) at 37° C. in aerobic conditions in a shaker at 150 rpm. *Candida albicans* (ATCC #18804) is grown in YM broth (Difco). Exponential cultures obtained by reculturing stationary overnight precultures were used for experiments.

*E. coli, P. aeruginosa*, and *S. aureus* are grown in fresh medium for approximately 1 hr to a density of about $10^8$ cells/ml; the OD values at 650 nm are 0.6, 0.8, and 0.8, respectively. *C. albicans* is grown for approximately 4 hr to an approximate density of $10^8$ cells/ml, corresponding to an OD of 6 at 650 nm (measured at 10-fold dilution). Cells were used for experiments in the mid-log growth phase.

2. Photosensitizers and Light Sources

Toluidine blue O (TBO), a common PS, is available from commercial sources, e.g., from Sigma (St. Louis, Mo.) and was dissolved in water to give a 1 mM stock solution that is stored in the dark at 4° C. for a maximum of 2 weeks.

A noncoherent lamp with filtered liquid light guides, e.g., a LumaCare™ LC122 lamp (MBG Technologies, Inc., Newport Beach, Calif.) was used to provide illumination of PS. More specifically, for illumination of fullerenes, a broadband white light band pass filter (400-700 nm) was used, whereas for TBO, a band pass filter at 620-650 nm was used. The lamp was adjusted to give a uniform spot of about 4 cm diameter with an irradiance of 200 mW/cm$^2$, as measured with a power meter, e.g., a model DMM 199 meter with 201 Standard head (Coherent, Santa Clara, Calif.).

3. Photodynamic Inactivation Studies

Typically, derivatized fullerenes prepared as described above are dissolved in DMSO to provide stock solutions having final concentrations of about 5 mM. Compound CI1 is poorly soluble; accordingly a concentration of 2.7 mM can be used. All stock solutions were stored in the dark at room temperature.

In some experiments, for example in studies described in Examples below, suspensions of *S. aureus* cells ($10^8$ per ml) were incubated with derivatized fullerenes such as NI-1-3 and CI1-3 at a concentration of 100 μM in PBS at room temperature for 10 min. In other experiments, the bacterial suspension was centrifuged (4000×g for 10 min) after incubation and resuspended in fresh PBS before illumination; the latter procedure was referred to herein as a "wash." *E. coli, P. aeruginosa*, and *C. albicans* were used at concentrations of about $10^8$ cells per ml.

Illumination was carried out from above on microbial cell suspensions in wells of a 24-well plate. Aliquots were removed at times corresponding to the delivery of calculated fluences of light, and were serially diluted in PBS and streaked on square BHI or YM agar plates according to the method of Jett et al. (Jett, B. D., Hatter, K. L., Huycke, M. M., and Gilmore, M. S. (1997). Simplified agar plate method for quantifying viable bacteria. *Biotechniques* 23, 648-650). Survival fractions were calculated with reference to cells incubated in PBS alone. Values on killing curves at 0 J/cm$^2$ represent the dark toxicity of the fullerenes or other PS tested. Control cells were treated with light and no PS and also analyzed for viability.

4. Mammalian Cell Culture Experiments

Experiments to test the effect of functionalized fullerenes on mammalian cells can be performed in a suitable mammalian cell line. One such cell line is the L929 murine fibroblast line (ATCC #CCL1), a spontaneously transformed immortalized cell line established from the normal subcutaneous areolar and adipose tissue of a male C3H/An mouse (Earle, W. R., Schilling, E. L., Stark, T. H., Straus, N. P., Brown, M. F., and Shelton, E. (1943). Production of malignancy in vitro. IV. The mouse fibroblast cultures and changes seen in the living cells. *J. Natl. Cancer Inst.* 4, 165-212). In a suitable assay, these cells were cultured in Dulbecco's modified Eagle's medium (Sigma) at 37° C. in a humidified atmosphere containing 5% CO2. The medium is preferably modified by using 4 mM L-glutamine (containing 1.5 g/l sodium bicarbonate and 4.5 g/l glucose), 10% fetal bovine serum (FBS), 100 U/ml penicillin, and 100 mg/ml streptomycin. Cells were plated in 96-well cell culture plates, at a density of about 300 cells/well, and are allowed to attach for 24 hr.

Fullerenes and other PS, e.g., TBO, were added at a concentration of about 10 μM in 200 μl complete medium per well. After 10 min, fresh medium is added, and the cultures were illuminated with white light (for fullerenes) or with red light (for TBO). At the completion of the illumination period, cells were returned to the incubator for 24 hr. Cell viability can be determined, for example, by using the MTT-microculture tetrazolium assay, a method of assessing cellular response to PDT (Merlin, J. L., Azzi, S., Lignon, D., Ramacci, C., Zeghari, N., and Guillemin, F. (1992). MTT assays allow quick and reliable measurement of the response of human tumour cells to photodynamic therapy. *Eur. J. Cancer* 28A, 1452-1458. This assay involves the reduction of a colorless substrate, i.e., 3-[4,5-Dimethylthiazol-2-yl]-diphenyltetrazolium bromide (Sigma, St. Louis, Mich.) to an insoluble dark-blue formazan product which is formed in proportion to the amount of succinate dehydrogenase activity in the mitochondria of living cells. After incubation with MTT for periods ranging from 4 to 8 hr, the medium was aspirated from each well, and 100 ml DMSO is added. The absorbance at 570 nm was read by a microplate reader, e.g., a Spectra Max™ 340 PC (Molecular Devices, Sunnyvale, Calif.). The fraction of cells surviving was calculated by dividing the mean absorbances of formazan produced from PDT-treated cells by the mean absorbances from dark controls incubated with PS and kept at room temperature for periods of time equal to the irradiation times.

5. Statistics

Preferably values are calculated and expressed as means and standard errors of at least six independent wells. Differences between killing curves were tested for significance at the highest comparable fluence by an unpaired two-tailed Student's t test, assuming equal or unequal variation in the standard deviations, as appropriate. P values of less than 0.05 were considered significant.

Example 8

Studies of Derivatized Fullerenes as Antimicrobial Photosensitizers

This Example describes a series of experiments performed to test the ability of certain embodiments of derivatized fullerenes, prepared as described above, to act as effective antimicrobial PS against a range of bacterial strains and yeast.

Four microbial species were used in this study. Briefly, *Escherichia coli* was purchased from ATCC (ATCC #25922), *Pseudomonas aeruginosa*, two clinical isolates, were obtained; UCBP PA 14 from L. Rahme (Massachusetts General Hospital) and PA 767K from Kim Lewis (Tufts University), slime deficient mutant of *Staphylococcus aureus* was obtained from Gerald B Pier (Channing Laboratories). Yeast strain *Candida albicans* was purchased from ATCC (ATCC #18804). Exponential cultures obtained by reculturing stationary overnight cultures were used for all experiments. Bacteria were grown at 37° C. in BHI broth to a cell density of $10^8$ cells per mL. *C. albicans* was grown 37° C. in YM medium to $10^7$ cells/mL.

Six fullerene derivatives (NI1-3 and CI1-3) were evaluated. Five of them were dissolved in DMSO to obtain a stock solutions of 5 μM, and one (CI1) was poorly soluble and therefore the concentration of the stock solution was 2.7 μM. Concentration of fullerene derivatives used in the experiments varied between 1 and 100 μM.

Fullerene derivatives were mixed with microbial suspensions and incubated in the dark at room temperature for 10 minutes. Excess fullerenes were either washed out of, or left in, the suspensions before illumination. Aliquots of 100 μL were placed on three well hanging drop slides and illuminated with either a 405-nm laser (Nichia Chemical Industries) at an irradiance of 100 mW/cm$^2$, or with white light at room temperature. White light was 400-700 nm Gaussian distribution from LumaCare™ lamp with filtered liquid light guide, as described above.

During illumination, aliquots of 20 μL were taken to determine the colony-forming units. The contents of the wells were mixed before sampling. The aliquots were serially diluted 10-fold in PBS without Ca$^{++}$/Mg$^{++}$ to give dilutions of $10^{-1}$-$10^{-6}$ times the original concentrations, and were streaked horizontally on square BHI agar plates. Plates were incubated at 37° C. overnight. Colonies were counted and survival fraction was determined as percent of survival compared to control. Microbial suspensions incubated with fullerene derivatives in DMSO in the absence of light and bacteria illuminated in the absence of fullerene derivatives were used as controls. Fullerene derivatives and DMSO were not toxic for microorganisms in the dark and light alone did not cause cell destruction.

Figure 2:
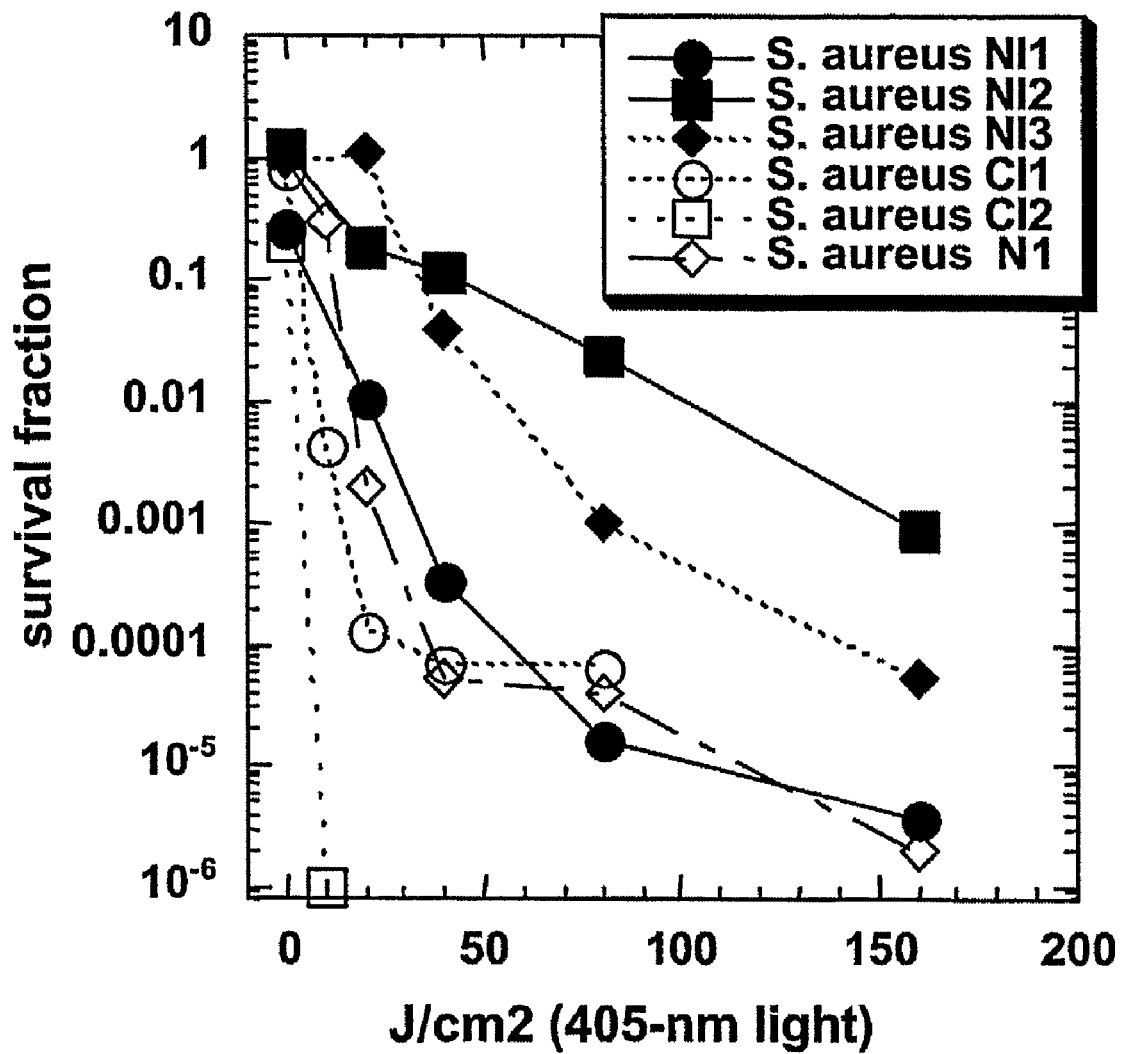
FIG. 2 is a graph illustrating photodynamic inactivation (PDI) of S. aureus bacteria by functionized fullerenes NI1-3 and CI1-3 prepared in accordance with the invention, following exposure to 405 nm light.

The ability of fullerenes NI1-3 and CI1-3 to mediate photodynamic inhibition (PDI) against the grain positive bacterium *S. aureus* was initially tested at 100 μM concentration for 10 minutes at light intensities (405 nm light) ranging from 0-200 J/cm$^2$. Referring now to FIG. 2, it is seen that all fullerene derivatives at this concentration have significant activity in mediating PDI of *S. aureus*; however CI2 is the most potent.

Figure 3:
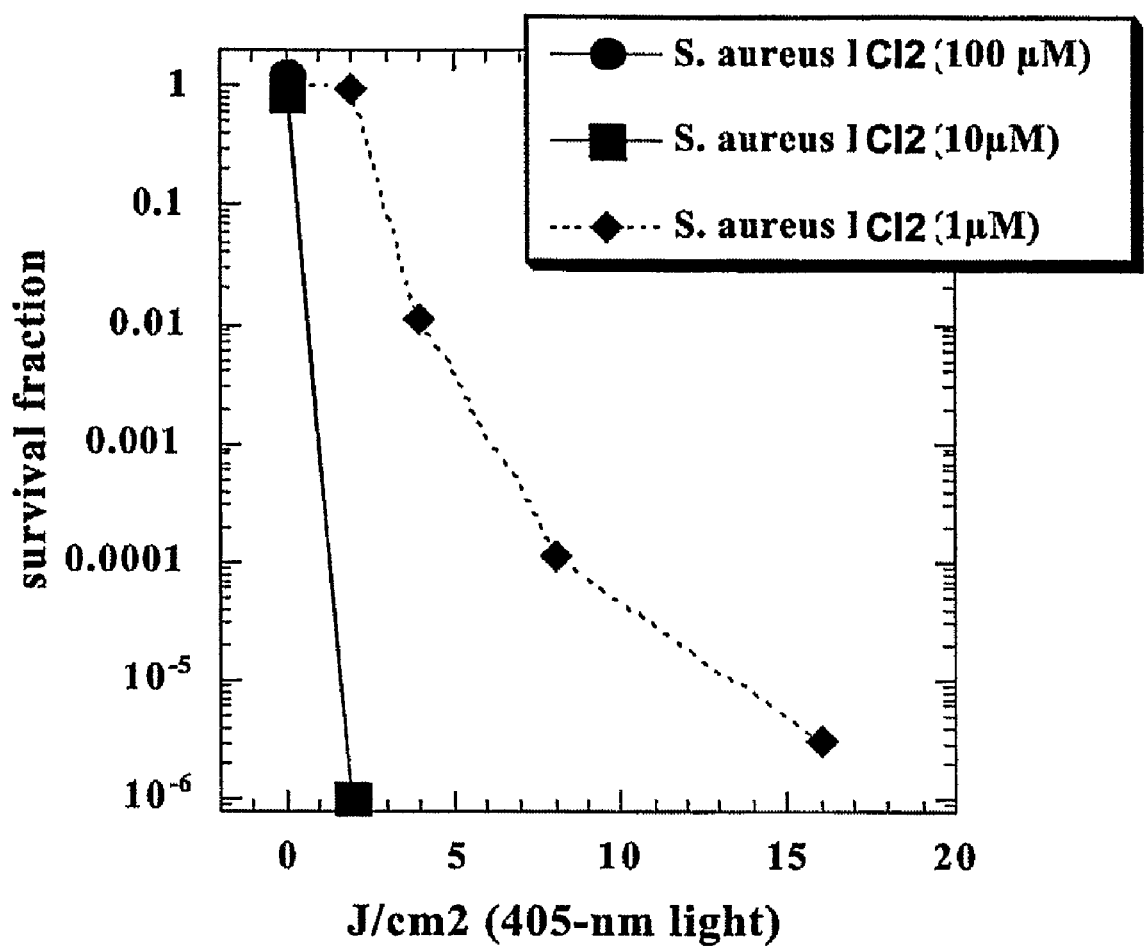
FIG. 3 is a dose-response curve illustrating PDI of S. aureus by varying concentrations of cationic fullerene CI2, in accordance with an embodiment of the invention.

Next, both the drug dose and the light dose were reduced in an assay using CI2 to determine the lowest effective PDT parameters for killing *S. aureus*. As can be seen from FIG. 3, substantial killing (6 logs) was achieved at 1-μM concentration of the functionalized fullerene exposed to light intensity of 8 J/cm$^2$ making CI2 approximately 1000 times more potent than the other fullerene derivatives.

Figure 4:
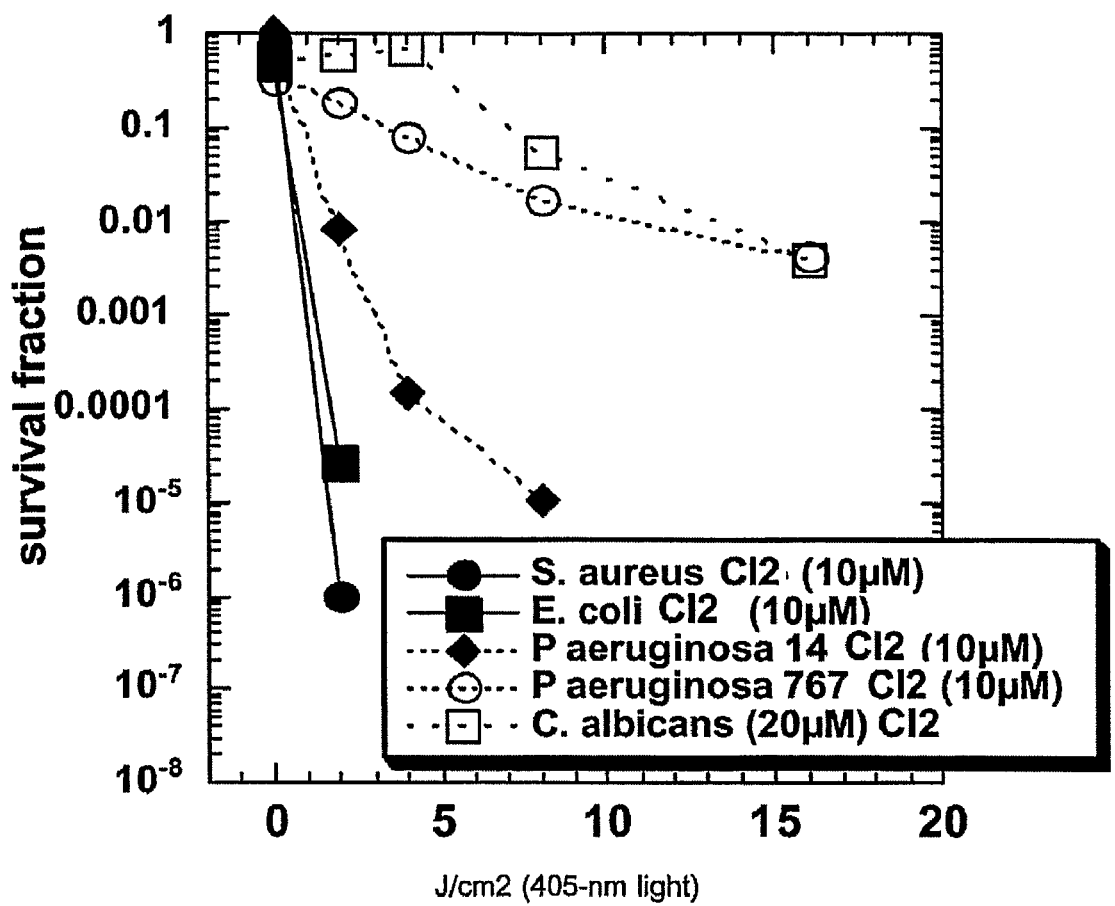
FIG. 4 is a graph showing PDI of several microbial species (bacteria—S. aureus, E. coli, P. aeruginosa; and yeast—C. albicans) by cationic fullerene CI2, in accordance with an embodiment of the invention.
Figure 5:
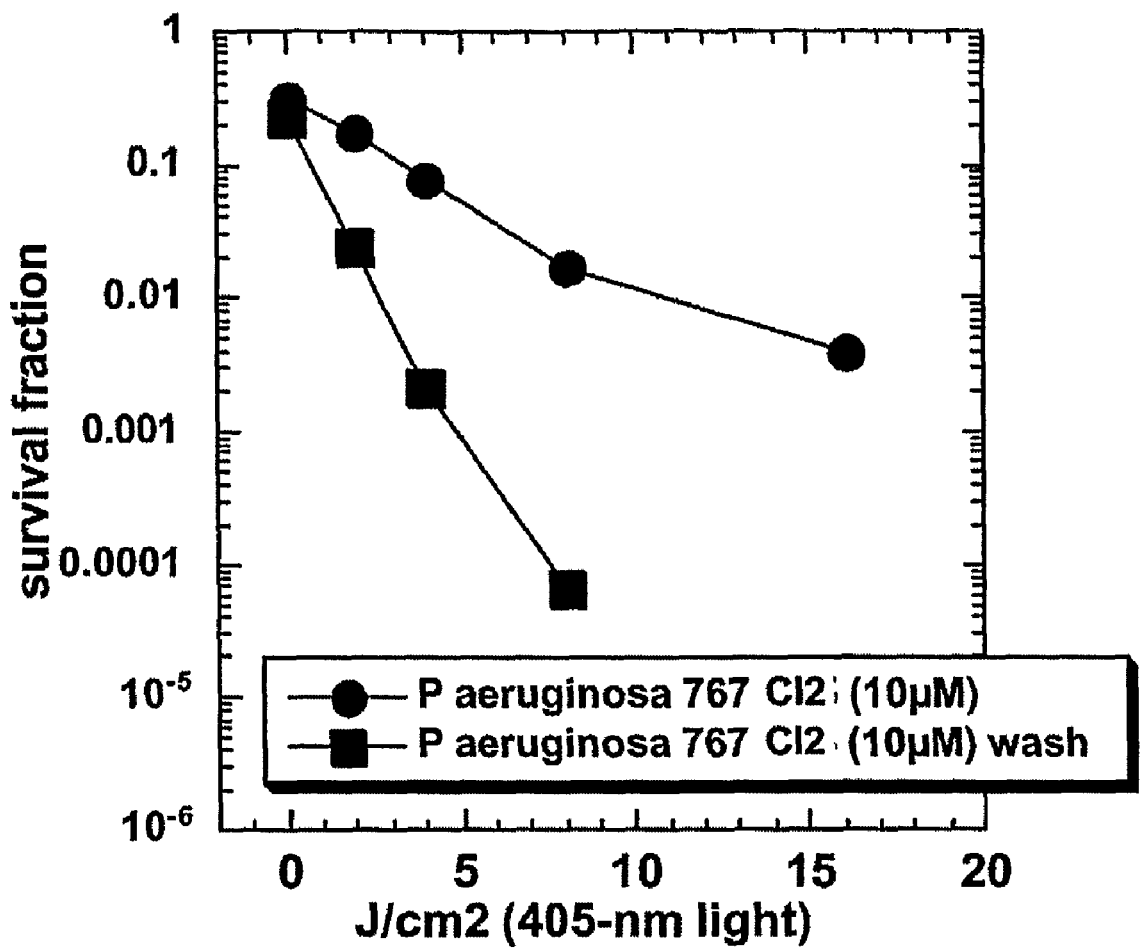
FIG. 5 is a graph showing effect of a wash procedure on PDI of P. aeruginosa by cationic fullerene CI2, in accordance with an embodiment of the invention.

The Gram-positive slime deficient *S. aureus* bacterium is very susceptible to PDT. The antimicrobial activity of CI2 was further defined by exploring its photokilling abilities with other pathogenic microorganisms including the Gram-negative bacterium *E. coli*, and the challenging *P. aeruginosa*, as well as the eukaryotic fungus *C. albicans*. Referring now to FIG. 4, it is seen that 10-20 μM concentration and 16 J/cm$^2$ of 405-nm light is sufficient to achieve high levels of killing of each of these pathogens. A comparison of the killing obtained by illuminating with and without a wash of the cells revealed more killing after a wash, as shown for *P. aeruginosa* in FIG. 5. This implies that the CI2 molecule is able to bind and penetrate the cell walls of these pathogens, rather than merely generating cytotoxic species outside of the cells.

Example 9

Selectivity of Cationic Fullerenes for Broad Spectrum Antimicrobial Photoinactivation While Sparing Mammalian Cells This Example describes PDI assays demonstrating that functionalized fullerenes in accordance with the present invention can effectively kill bacteria and yeast strains while sparing mammalian cells.

Mammalian cells used in these studies are a transformed mouse fibroblast cell line (L929) described above. Microbes studied included bacterial strains *S. aureus*, *E. coli*, and *P. aeruginosa*, and yeast strain *C. albicans*. All microbes and cells were cultured as described in Example 7 above. The concentration of fullerene derivatives was 10 μM for all cells and microbes except *S. aureus*, for which the concentration was reduced to 1 μM. Incubation time was 10 minutes in all cases. The survival fraction at 0 J/cm2 gives "dark" toxicity of fullerene. It should be noted that MTT assay used for mammalian cells does not have as big a dynamic range as CFU assay used for microbes.

Figure 6:
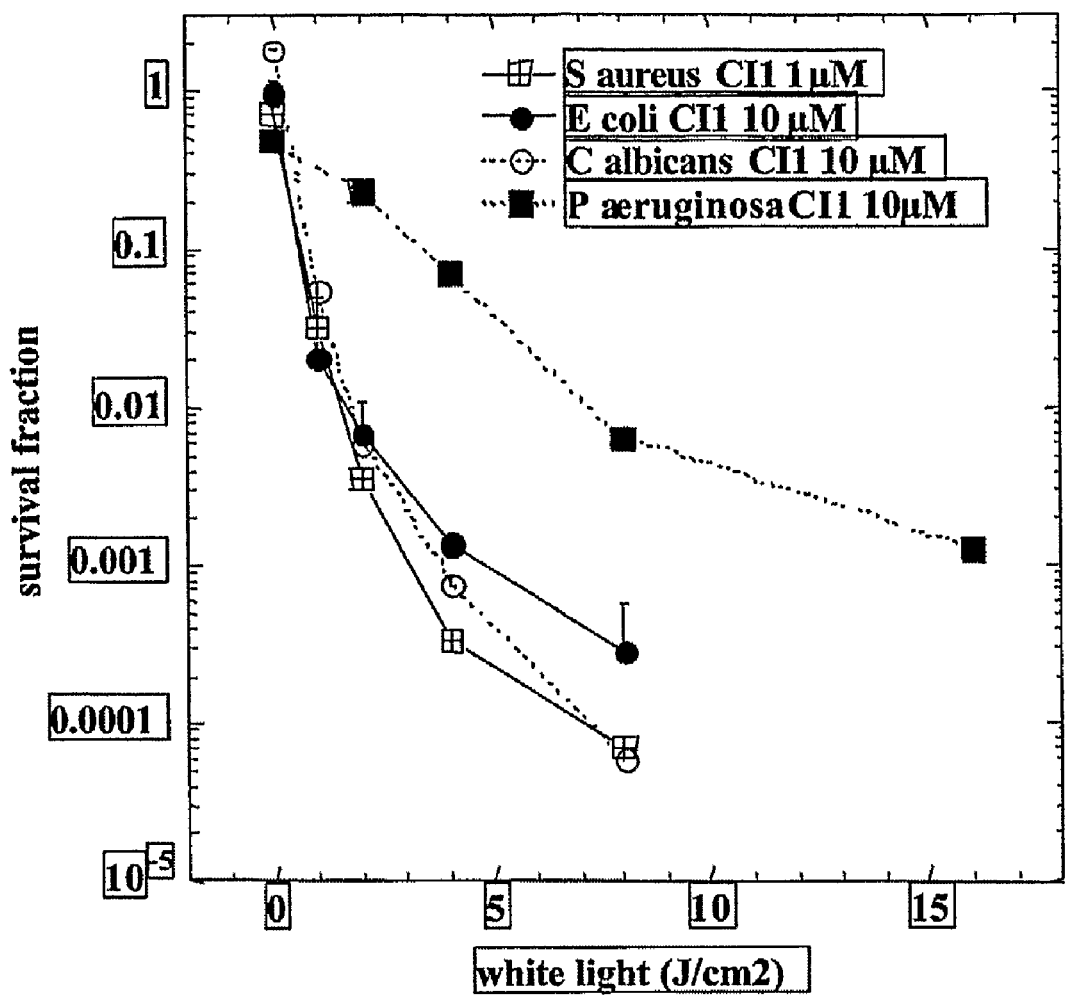
FIG. 6 is a graph showing PDI of bacterial strains S. aureus, E. coli, and P. aeruginosa and yeast strain C. albicans by cationic fullerene CI1 following exposure to low levels of white light.
Figure 7:
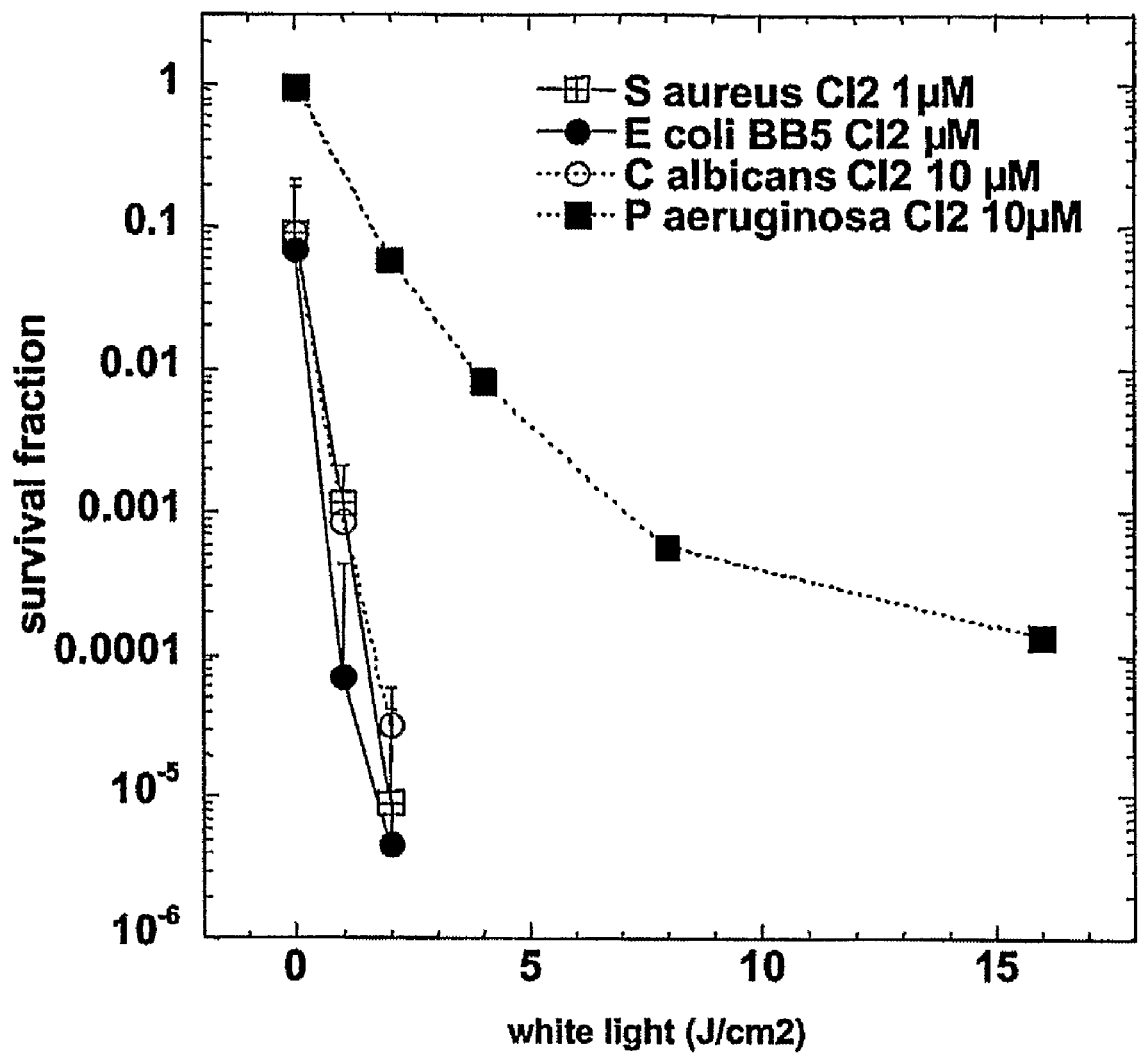
FIG. 7 is a graph showing PDI of bacterial strains S. aureus, E. coli, and P. aeruginosa and yeast strain C. albicans by cationic fullerene CI2, following exposure to low levels of white light.
Figure 8:
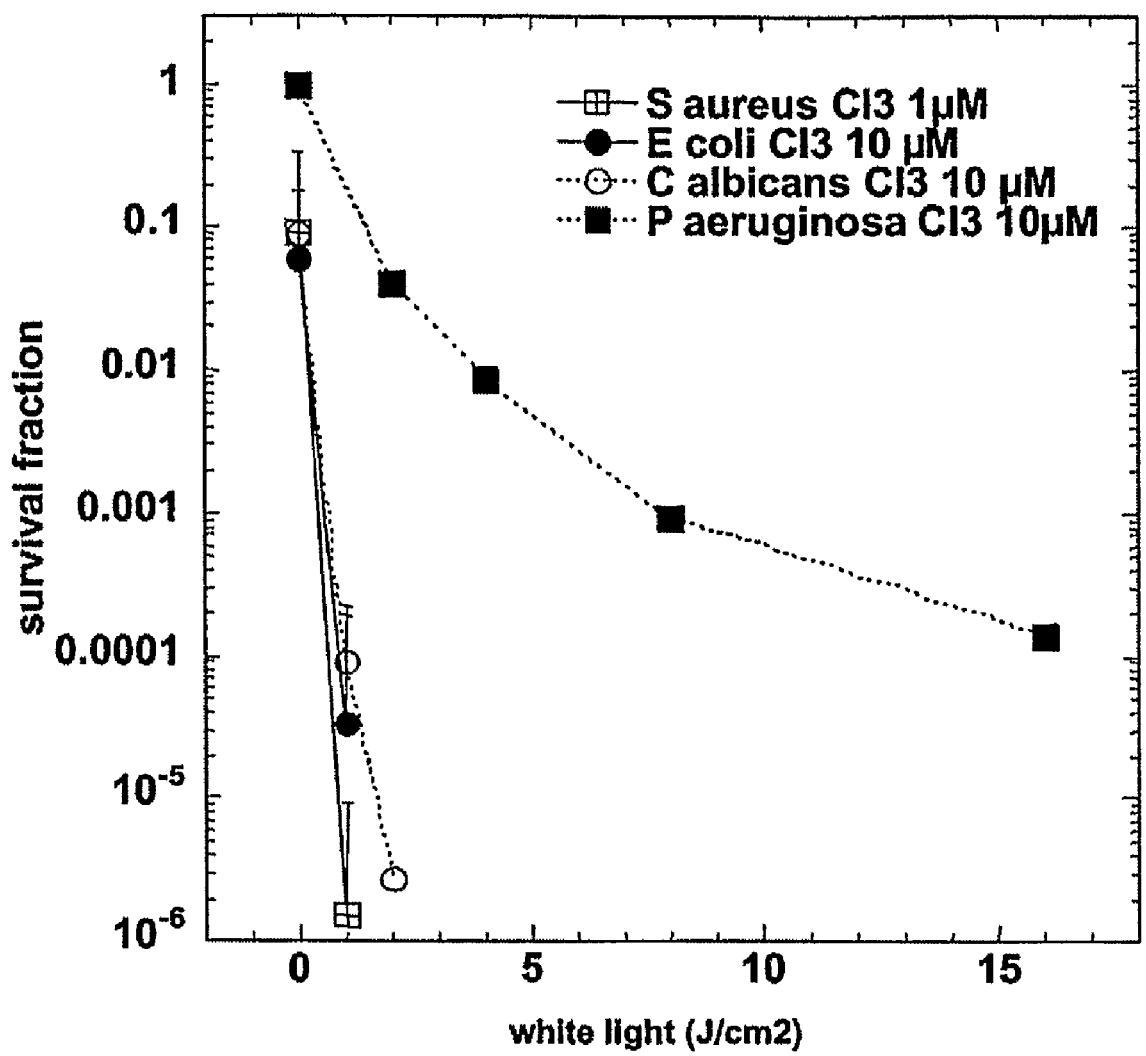
FIG. 8 is a graph showing PDI of bacterial strains S. aureus, E. coli, and P. aeruginosa and yeast strain C. albicans by cationic fullerene CI3, following exposure to low levels of white light.
Figure 9:
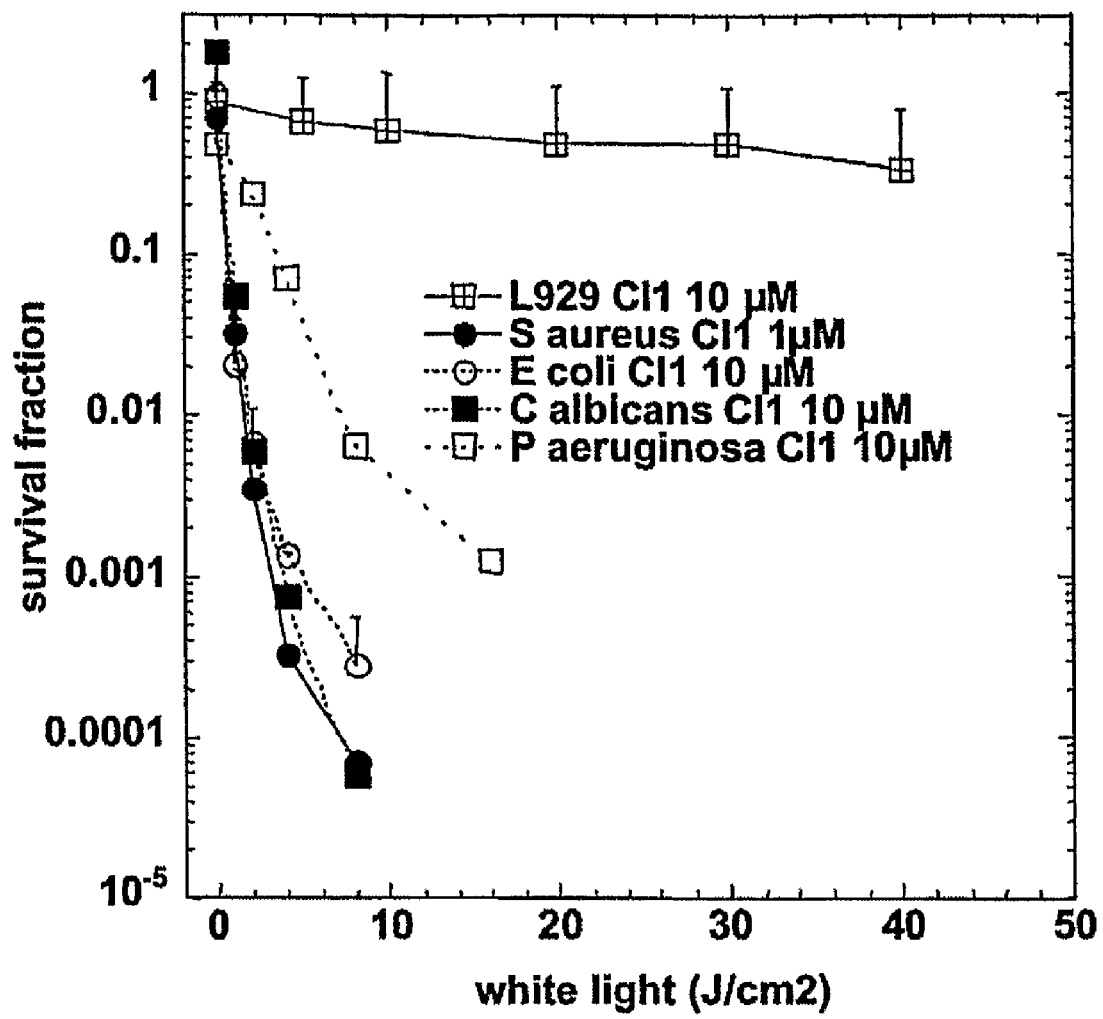
FIG. 9 is a graph showing PDI of bacterial strains S. aureus, E. coli, and P. aeruginosa, yeast strain C. albicans, and mammalian fibroblast cell line L929 by cationic fullerene CI1, following exposure to higher levels of white light than provided in FIGS. 6-8.
Figure 10:
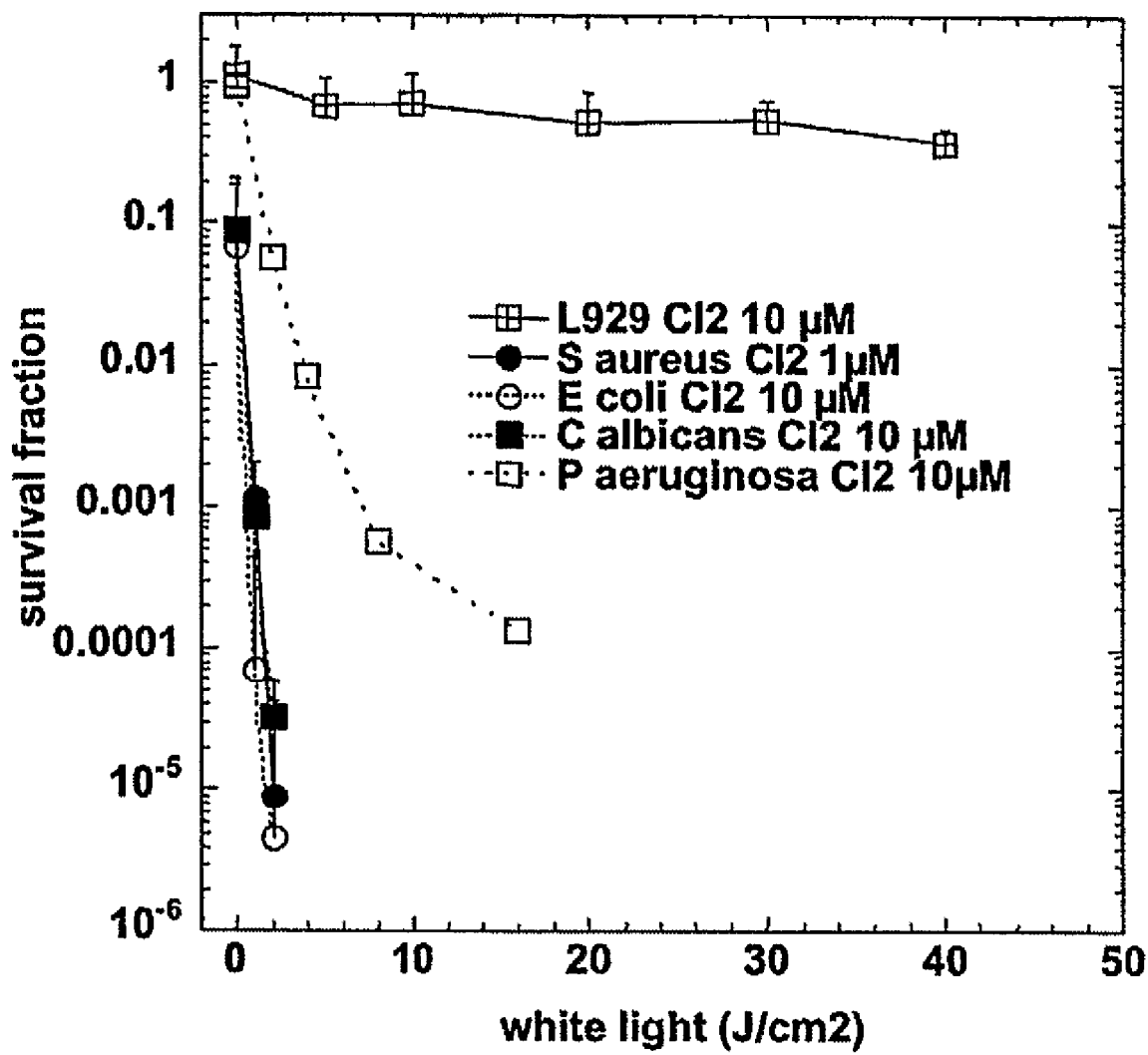
FIG. 10 is a graph showing PDI of bacterial strains S. aureus, E. coli, and P. aeruginosa, yeast strain C. albicans, and mammalian fibroblasts by cationic fullerene CI2, following exposure to white light under conditions as described for FIG. 9.
Figure 11:
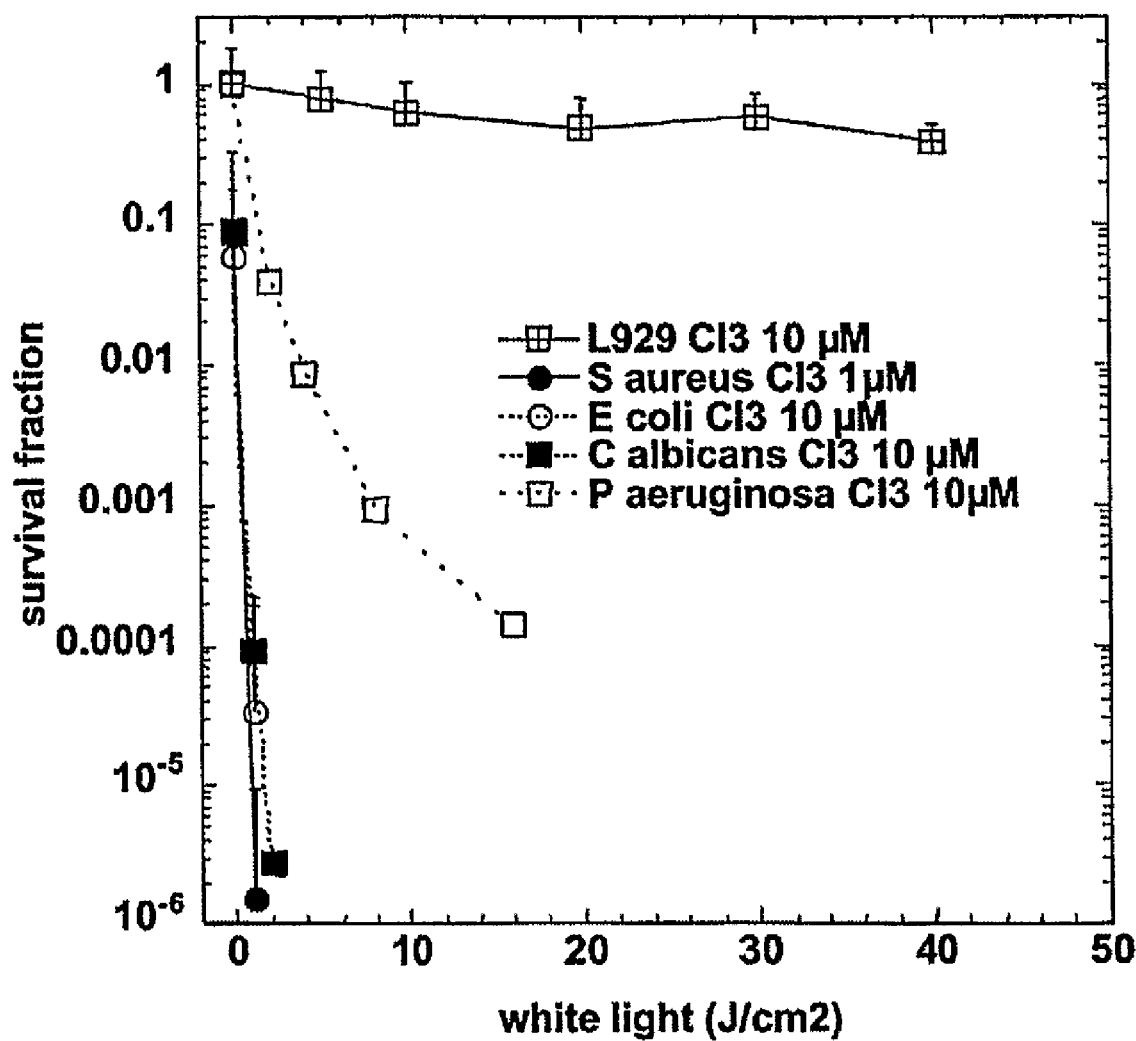
FIG. 11 is a graph showing PDI of bacterial strains S. aureus, E. coli, and P. aeruginosa, yeast strain C. albicans, and mammalian fibroblasts by cationic fullerene CI3, following exposure to white light under conditions as described for FIG. 9.
Figure 12:
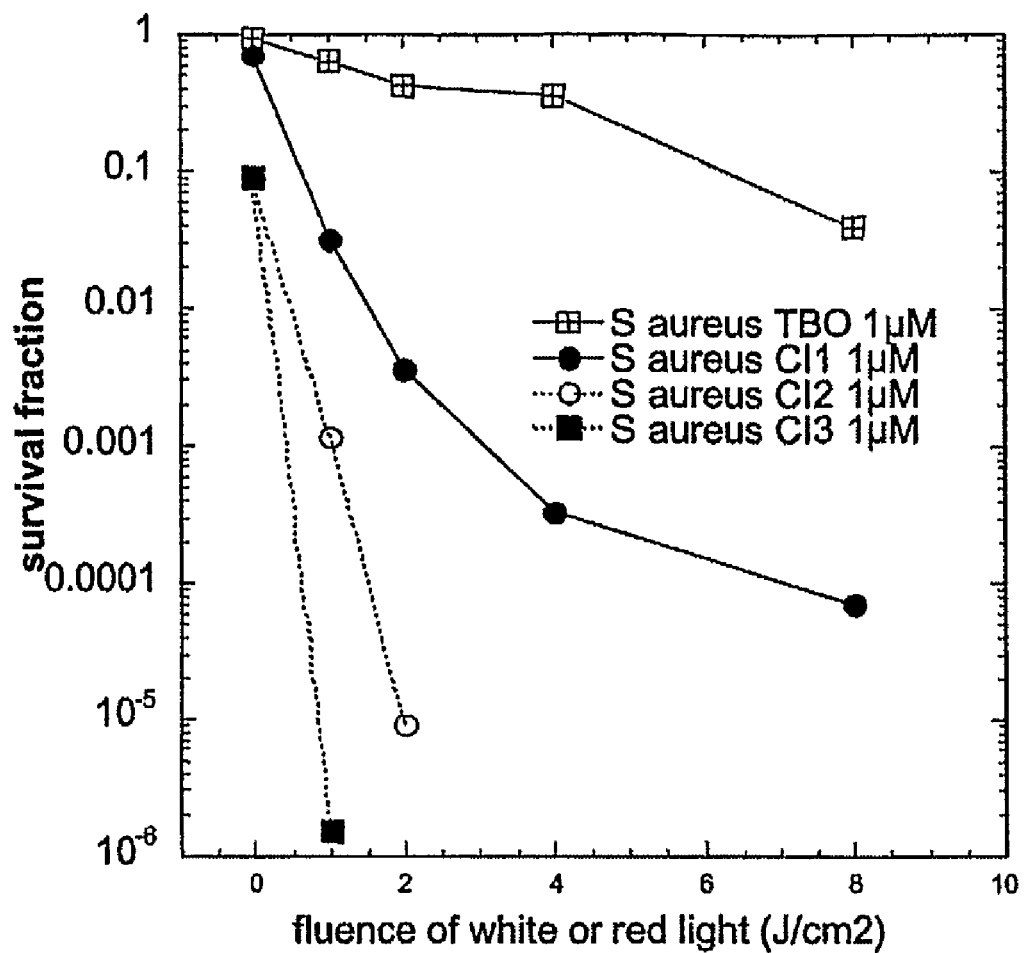
FIG. 12 is a graph showing PDI of bacterial strain S. aureus by cationic fullerenes CI1-3 in accordance with the invention, relative to that of known antimicrobial photosensitizer toluidine blue O (TBO).
Figure 13:
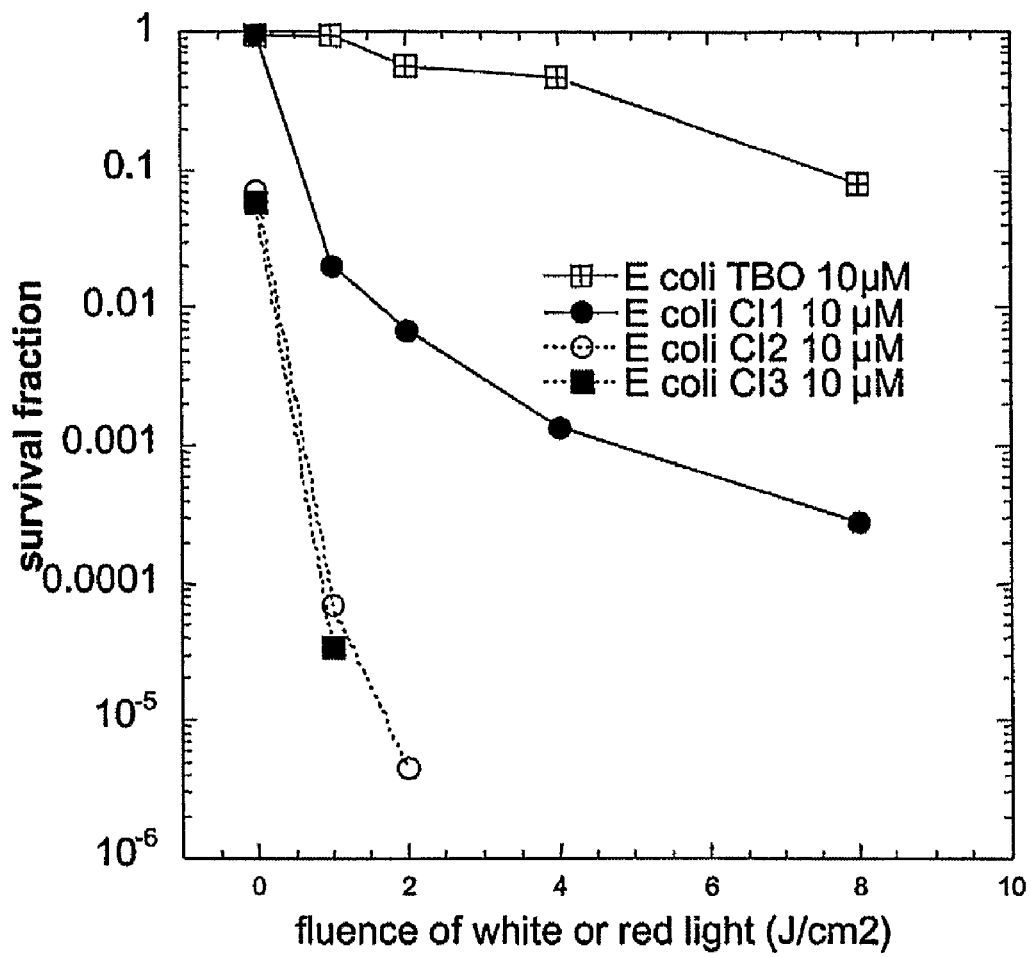
FIG. 13 is a graph showing PDI of bacterial strain E. coli by cationic fullerenes CI1-3 in accordance with the invention, relative to that of TBO.
Figure 14:
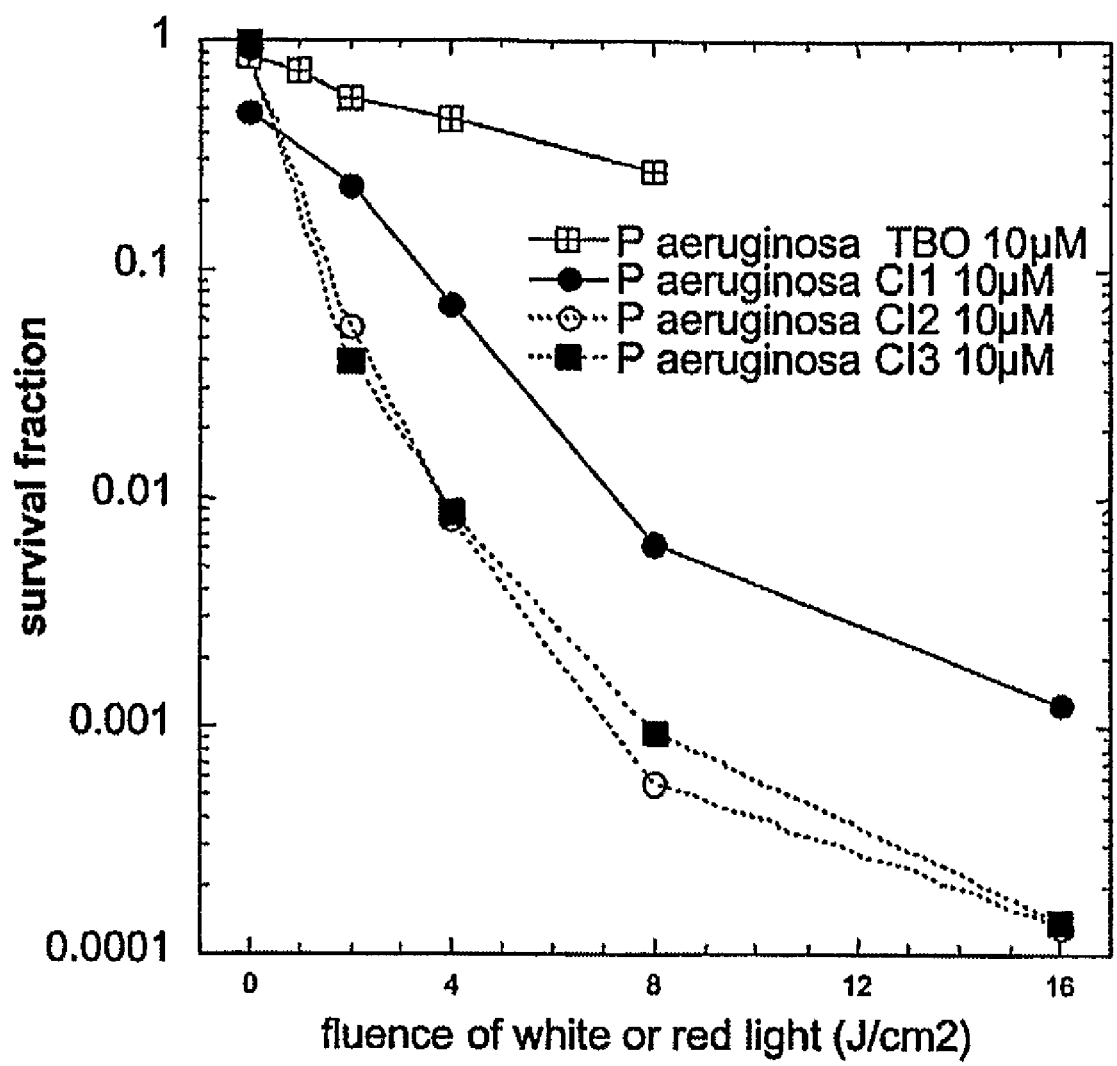
FIG. 14 is a graph showing PDI of bacterial strain P. aeruginosa by cationic fullerenes CI1-3 in accordance with the invention, relative to that of TBO.
Figure 15:
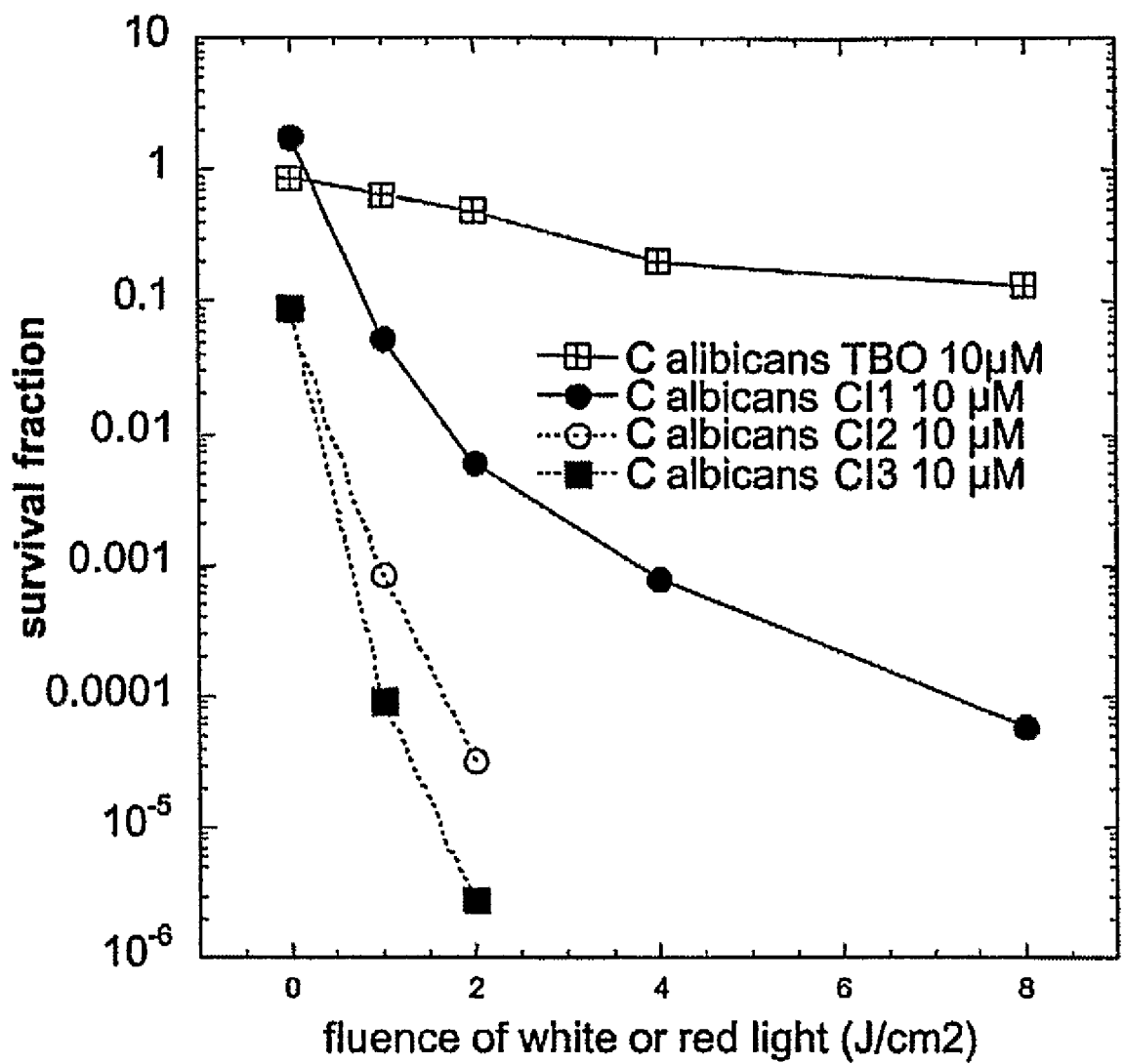
FIG. 15 is a graph showing PDI of yeast strain C. albicans by cationic fullerenes CI1-3, in accordance with the invention, relative to that of TBO.

FIGS. 6 to 8 show the PDT activity of CI1, CI2, and CI3 cationic fullerenes against various microorganisms at fluences of 0-15 J/Cm$^2$ of white light. FIGS. 9 to 11 illustrate results with CI1, CI2, and CI3 at fluences uo to 50 J/Cm$^2$ of white light. As can be seen in these data graphs, mammalian cells are not killed by this regimen whereas the microbes are effectively killed. Further studies demonstrating selectivity of derivatized fullerenes in accordance with the invention for killing microbial, as opposed to mammalian, cells, are described in Examples 11 and 15 below.

Example 10

Comparison of Cationic Fullerenes with Toluidine Blue O (TBO) for Broad Spectrum Antimicrobial Photoinactivation This Example describes studies undertaken to compare the killing efficiency of cationic fullerenes of the present invention with that of toluidine blue O (TBO), a well-known antimicrobial photosensitizing agent.

TBO is used extensively for photodynamic inhibition (PDI), as discussed in many reported studies. For example, TBO has been investigated for use in treating the gum disease gingivitis (caused by bacteria) and other pathogenic oral bacteria, *E. coli* O157:H7 and *Listeria monocytogenes*, buccal mucosa (in rats), multi-drug resistant malignancies, *Helicobacter pylori*, and human leukaemic T cells. Thus, a comparison of fullerene-based PS in accordance with the invention with TBO provides a measure of efficacy as compared with that of a well-used and understood PS. This compound was chosen not only because it is widely used in PDI studies, but also because it is cationic (like CI1-3) and accordingly should associate with the negatively charged cell walls of bacterial pathogens.

In order to obtain a comparison of the CI1-3 photosensitizers with TBO, PDI experiments were conducted with CI1-3 compounds and TBO at identical concentrations. In these studies, the concentration of fullerene derivatives or TBO was 10 μM for all microbes except *S. aureus* where concentration was reduced to 1 μM. Incubation time was 10 minutes in all cases. Survival fraction at 0 J/cm2 gives "dark" toxicity of fullerene derivatives or TBO. Broad band white light was used for fullerene derivatives (400-700 nm) and 620-650 nm red light was used for TBO.

Referring to FIGS. 12-15, it can be seen that under the same conditions, all three of the tested cationic compounds, i.e., CI1-3, exhibited PDI of the four microorganisms investigated (*E. coli, P. aeuriginosa, S. aureus*, and *C. albicans*) that is far superior to that of TBO. See also Example 14, infra.

Example 11

Mammalian Cell Toxicity of Fullerenes Relative to TBO

This Example demonstrates that fullerene-based PS agents in accordance with the present invention are less toxic at high light levels than is the commonly used photosensitizer toluidine blue O (TBO).

At the fluences used to carry out PDI of pathogens, the CI-3 cationic PS exhibited negligible toxicity to L929 mammalian cells (see, for example, FIGS. 9-11). Nevertheless, the toxicity at high fluences was compared with that of TBO, which is one of the few PS compounds that also exhibits relatively low mammalian toxicity.

Figure 16:
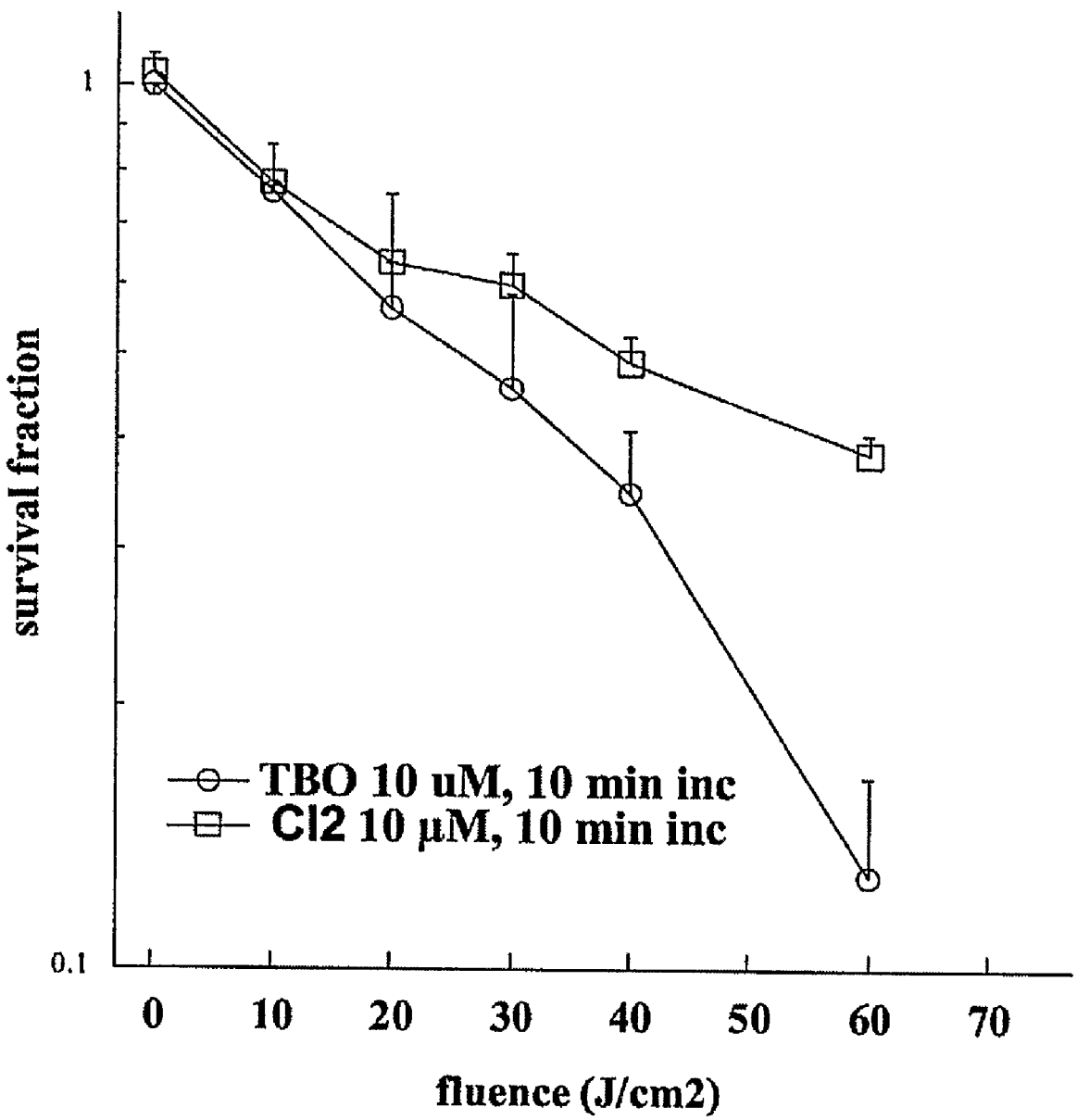
FIG. 16 is a graph showing PDI at high light levels of mammalian fibroblasts by cationic fullerene CI2 in accordance with the invention, relative to TBO.

Remarkably, as shown in FIG. 16, results of this study show that CI2 is considerably less toxic to mammalian cells at high fluences than TBO, making it superior not only in PDI but also in its selectivity for microbes. See also Example 15, infra.

Example 12

Screening of Derivatized Fullerenes as Antimicrobial PS

This Example describes further characterization of embodiments of functionalized (derivatized) fullerenes in accordance with the present invention with respect to their ability to mediate photodynamic inhibition (PDI) against gram-negative and gram-positive bacteria.

Derivatized fullerenes NI1-3 and CI1-3 were prepared as described above and used in assays to assess their potential to mediate PDI against the gram-positive bacterium *S. aureus* after 10 min incubations with 100 µM concentrations of fullerenes under conditions of "no wash," or "wash," i.e., with or without centrifugation to remove the bacteria after the 10 minute incubation and resuspension in fresh PBS before illumination, as described above.

Figure 17A:
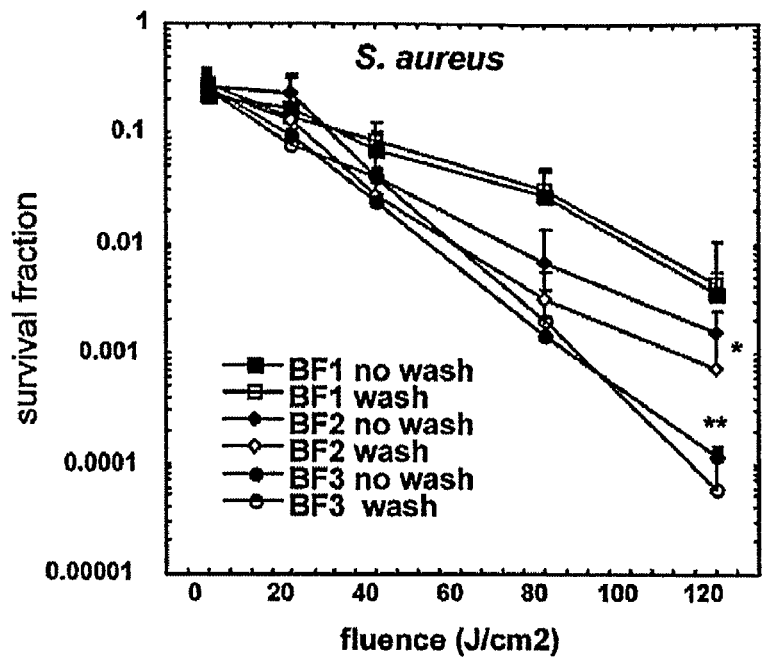
FIGS. 17A and B are two graphs showing PDI of S. aureus (A) and E. coli (B) bacteria by nonionic fullerenes NI1-3 in accordance with the invention, under conditions with or without washing to remove fullerenes prior to illumination.

The results of these experiments are shown in FIG. 17A. More particularly, FIG. 17A shows results of experiments in which *S. aureus* ($10^8$ cells per ml) were incubated as described, then followed (or not followed) by a wash, i.e., centrifugation and resuspension as described, and subsequent illumination with 400-700 nm light at an irradiance of 200 mW/cm$^2$. Aliquots were removed from the suspension after the various fluences of light (0-120 J/cm$^2$) had been delivered and the CFU had been determined. Values shown in FIG. 17 are means of six independent experiments and bars are SEM. Single asterisks (*) denote $p<0.05$; double asterisks (**) denote $p<0.01$ by two-tailed unpaired t test.

From the results of "no wash" experiments, it was seen that compounds CI2 and CI3 were completely dark toxic to *S. aureus* and gave zero colonies or >99.9999% killing, regardless of the amount of light delivered. Compound CI1 showed significant dark toxicity (99%; e.g., see first point of curve with squares in FIG. 18). Referring again to FIG. 17, by contrast, compounds NI1-3 show only minor dark toxicity toward *S. aureus* (i.e., 60%-80%; see FIG. 17A).

When relatively large fluences of broad-band white light were delivered to bacterial suspensions still containing the fullerenes, a fluence-dependent loss of viability of *S. aureus* ranging from 2-4 logs of killing was observed, as shown in FIG. 17A (closed symbols). Compounds NI1-3 displayed significant differences in effectiveness between members of the series. Their effectiveness was NI3>NI2>NI1, and the differences in the survival fraction were significant ($p<0.05$) at the two highest fluences (80 and 120 J/cm$^2$) (FIG. 17A).

In order to test whether the fullerenes actually bound to the bacterial cells, PDI was compared with and without a wash as described. As can be seen by comparing curves with open and closed symbols in FIG. 17A, there was no difference in killing with and without a wash, indicating that the fullerenes bound to the bacteria, and could not easily be washed out.

Figure 17B:
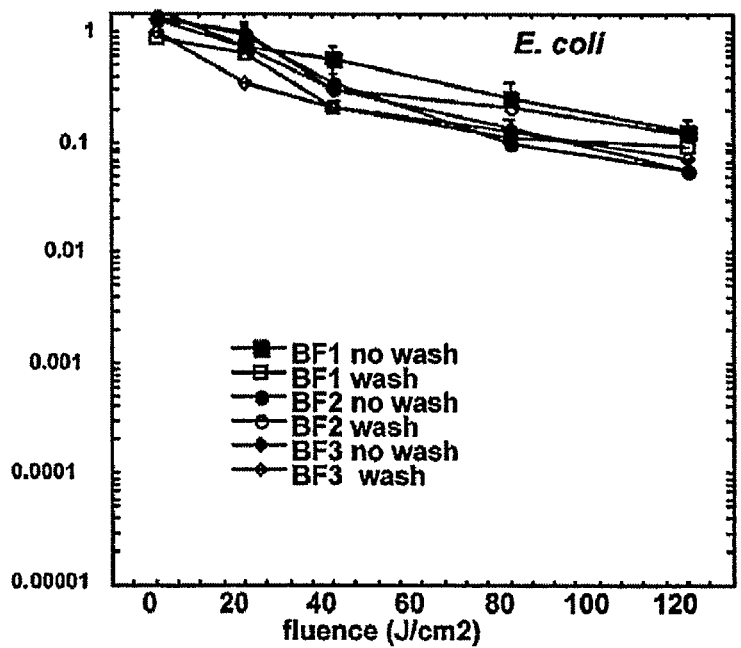

Compounds NI1-3 were also tested under the same conditions (100 µM incubation for 10 min without wash) with the gram-negative bacteria *E. coli*. Referring to FIG. 17B, it is seen that there was no dark toxicity and only a very small amount of light-mediated killing (less than 90%). NI1 was significantly less effective than NI2-3 ($p<0.05$).

Example 13

Figure 18:
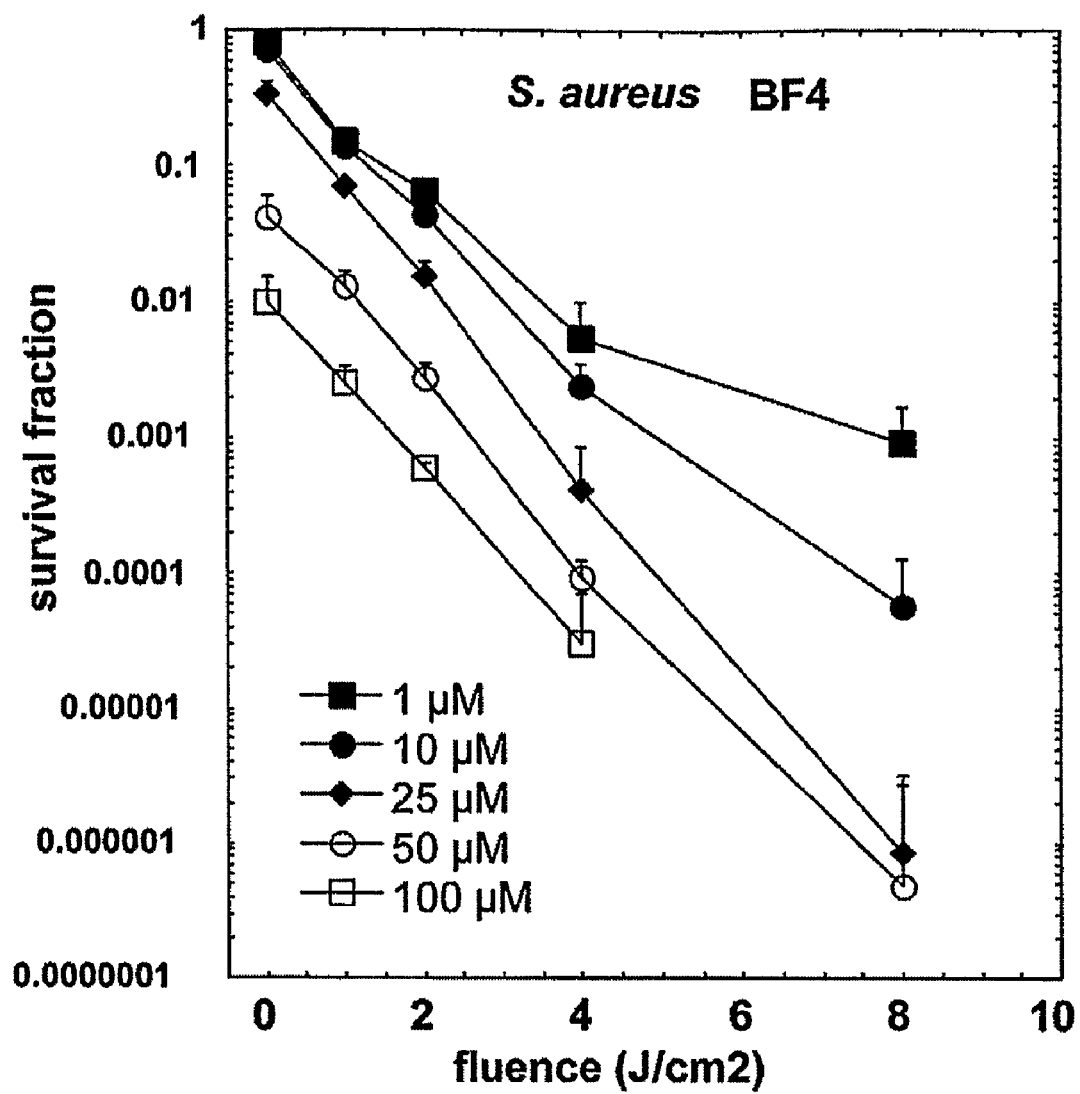
FIG. 18 is a graph showing PDI of S. aureus with cationic fullerene CI1 at specified concentrations, in accordance with an embodiment of the invention.

Cationic Fullerenes Mediate Photodynamic Inactivation of Three Microbial Classes Compound CI1 showed significant dark toxicity toward *S. aureus* at 100 µM; therefore the concentration of CI1 was decreased in the incubation mixture in a step-wise manner to 50, 25, 10, and 1 µM. These experiments, carried out with a wash, are illustrated in FIG. 18. More particularly, FIG. 18 shows PDI of *S. aureus* under the specified conditions, followed by a wash and illumination with white light. Values in the graphs represent means of six independent experiments and the bars are SEM.

As is shown in FIG. 18, the dark toxicity decreased as the concentration was decreased until, at 10 and 1 µM, dark toxicity was nonexistent. When PDI experiments were carried out after incubation of *S. aureus* with these concentrations of CI1, a fluence-dependent loss of viability was observed in all cases with comparatively low doses of light (4-8 J/cm2). Remarkably, the PDI killing curves were not significantly different among the different concentrations (compare the slopes of curves in FIG. 18). The difference between the curves was solely in the survival fraction at 0 J/cm$^2$, i.e., the dark toxicity.

Since an initial screening experiment had suggested that the bis- and tris-cationic fullerenes CI2 and CI3 would be more potent than CI1 (higher dark toxicity), they were tested against *S. aureus* at 1 µM with a wash. These results are shown in FIG. 19A.

More particularly, and for comparison, FIGS. 19A-B and 20A-B show PDI of various bacteria and yeast tested with cationic fullerene derivatives CI1-3 as follows—(FIG. 19A): *S. aureus* incubated with a 1 µM concentration of CI1-3; (FIGS. 19B, 20A, B): *E. coli*, (19B), *C. albicans* (20A), and *P. aeruginosa* (20B), all at $10^8$ cells per ml, incubated with CI1-3 at 10 µM concentrations for 10 min, followed by a wash and illumination with white light. Values are means of six independent experiments, and bars are SEM. *$p<0.05$, $p<0.01$, *$p<0.001$, by two-tailed unpaired t test.

Figure 19A:
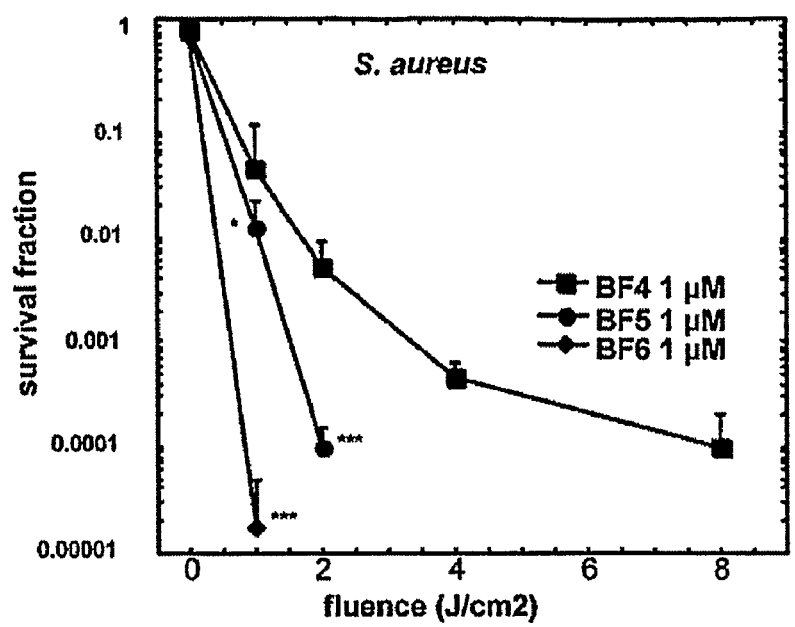
FIGS. 19A-B are two graphs showing PDI of S. aureus (A) and E. coli (B) with cationic fullerenes CI1-3, in accordance with an embodiment of the invention.

As shown in FIG. 19A, compounds CI2 and CI3 were highly active, with 2 and 1 J/cm$^2$ of light being sufficient to kill 4-5 logs, respectively. All three killing curves were significantly different ($p<0.01$).

Figure 19B:
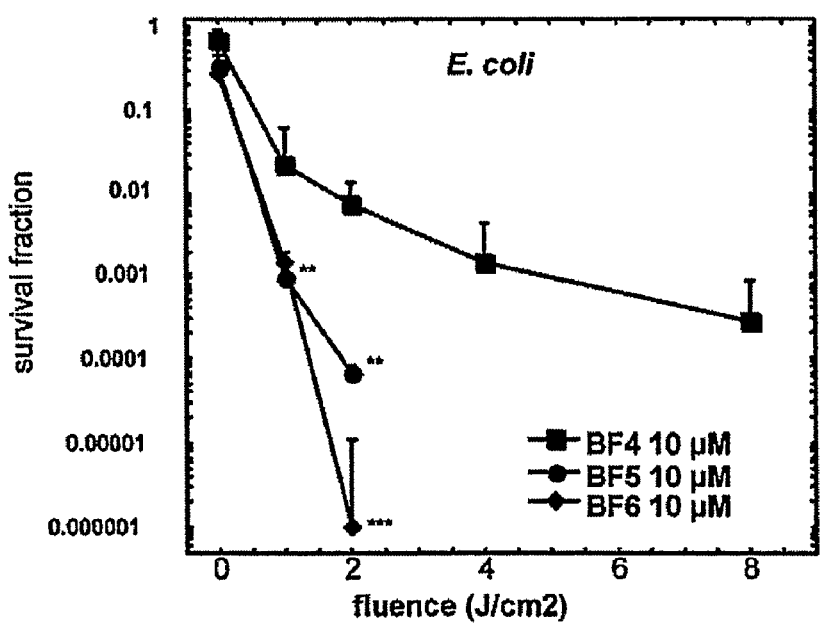

As it is known that gram-positive bacteria are much more susceptible to PDI than gram-negative bacteria or fungal species (Malik, Z., Ladan, H., and Nitzan, Y. (1992). Photodynamic inactivation of Gram-negative bacteria: problems and possible solutions. *J. Photochem. Photobiol.* B 14, 262-266, Nitzan, Y., Gutterman, M., Malik, Z., and Ehrenberg, B. (1992). Inactivation of Gram-negative bacteria by photosensitized porphyrins. *Photochem. Photobiol.* 55, 89-96), the cationic fullerenes CI1-3 were tested against other microorganisms, at a concentration of 10 µM with a wash. FIG. 19B shows the light-mediated killing of gram-negative *E. coli* with the three cationic fullerenes. It can be seen that CI2 and CI3 were highly effective, with 2 J/cm$^2$ giving 4 and 6 logs of killing, respectively. CI1 was much less potent, requiring 8 J/cm$^2$ to give 3 logs of killing (p<0.001). There was only minimal dark toxicity.

Figure 20A:
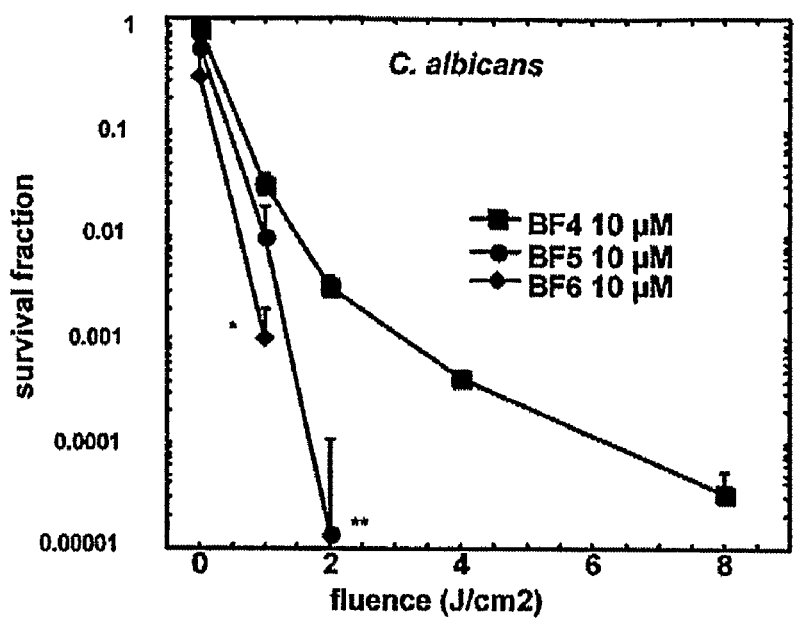
FIGS. 20A-B are two graphs showing PDI of C. albicans (A) and P. aeruginosa (B) with cationic fullerenes CI1-3, in accordance with an embodiment of the invention.

Referring now to FIG. 20A, it is shown that effective killing was also achieved against the yeast *C. albicans*, in which CI3 was slightly more effective than CI2 and both were much better than CI1 (p<0.001).

Figure 20B:
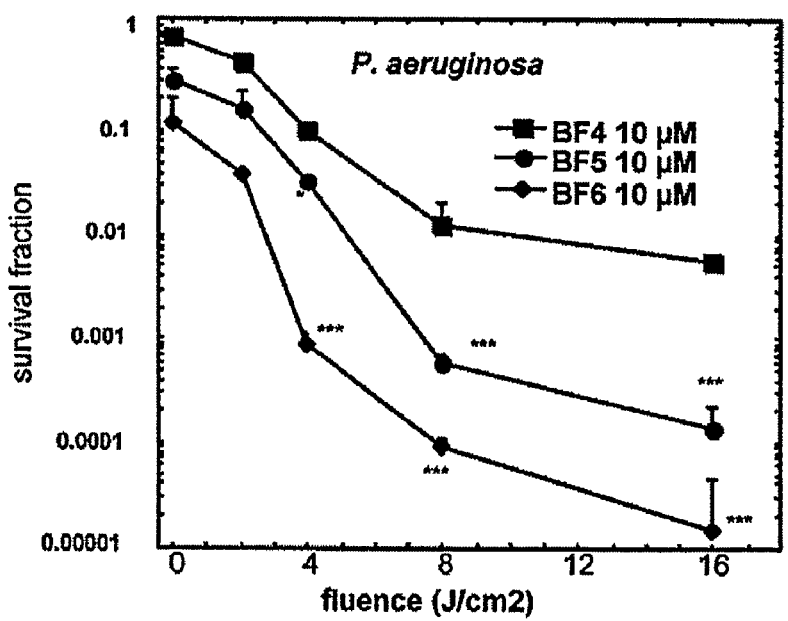

As shown in FIG. 20B, the gram-negative bacterium *P. aeruginosa* was more resistant than the other organisms tested. The maximum light dose delivered was doubled to 16 J/cm$^2$ in an effort to increase killing, but this had only a minimal effect. CI2 and CI3 were able to kill 3-5 logs, whereas CI1 gave 2 logs of killing of *P. aeruginosa*.

Example 14

Comparison of PDI Mediated by Photosensitizers CI1-3- and Toluidine Blue O

This Example describes experiments to compare PDI of gram-negative bacteria by the derivatized cationic fullerenes of the present invention with known photosensitizer TBO in the presence of serum.

In order to obtain an objective measure of how cationic fullerenes performed as antimicrobial photosensitizers, they were compared as above with a widely used phenothiazinium dye, i.e., TBO. In order to be able to directly compare the PDI-mediated killing of bacteria with killing of mammalian cells by photodynamic therapy (PDT), 10% serum was added to the bacterial suspension, because this is the standard growth condition used for mammalian fibroblasts. It has previously been shown that the addition of serum to bacterial PS incubations significantly reduces the effectiveness of the PS, probably because the PS binds to serum proteins, thus reducing the effective concentration available to bind to bacteria (Wilson, M., and Pratten, J. (1995). Lethal photosensitisation of *Staphylococcus aureus* in vitro: effect of growth phase, serum, and pre-irradiation time. *Lasers Surg. Med.* 16, 272-276, Lambrechts, S. A., Aalders, M. C., Verbraak, F. D., Lagerberg, J. W., Dankert, J. B., and Schuitmaker, J. J. (2005). Effect of albumin on the photodynamic inactivation of microorganisms by a cationic porphyrin. *J. Photochem. Photobiol.* B 79, 51-57).

In these experiments, the PDI of *E. coli* was tested using CI1-3 and TBO under the same conditions (i.e., at 10 µM concentration, for a 10 min incubation in the presence of 10% FBS, followed with a wash).

Figure 21A:
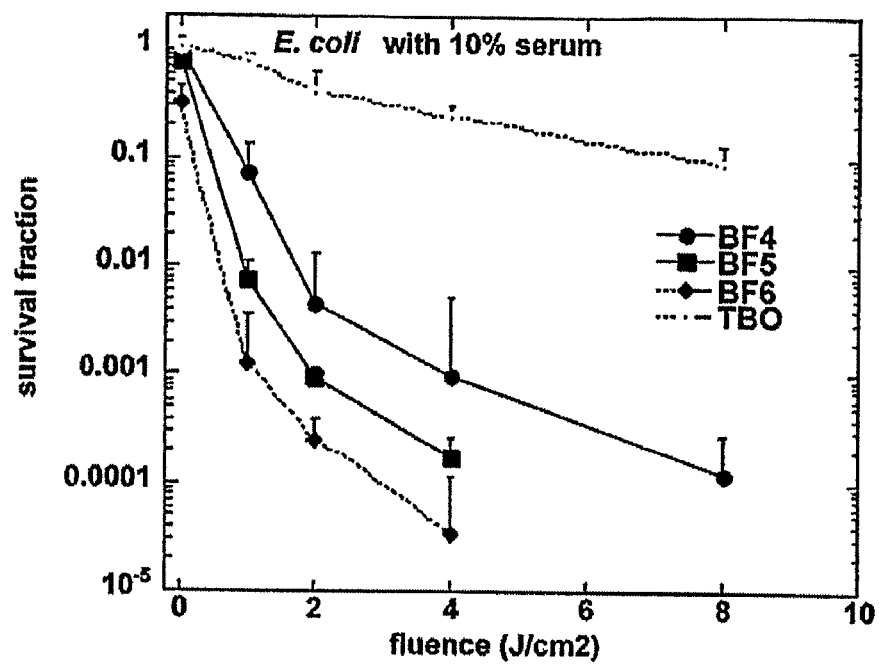
FIGS. 21A-B are two graphs showing PDI of E. coli (A) and mammalian fibroblasts (B) under the same conditions with cationic fullerenes CI1-3, in accordance with an embodiment of the invention.
Figure 21B:
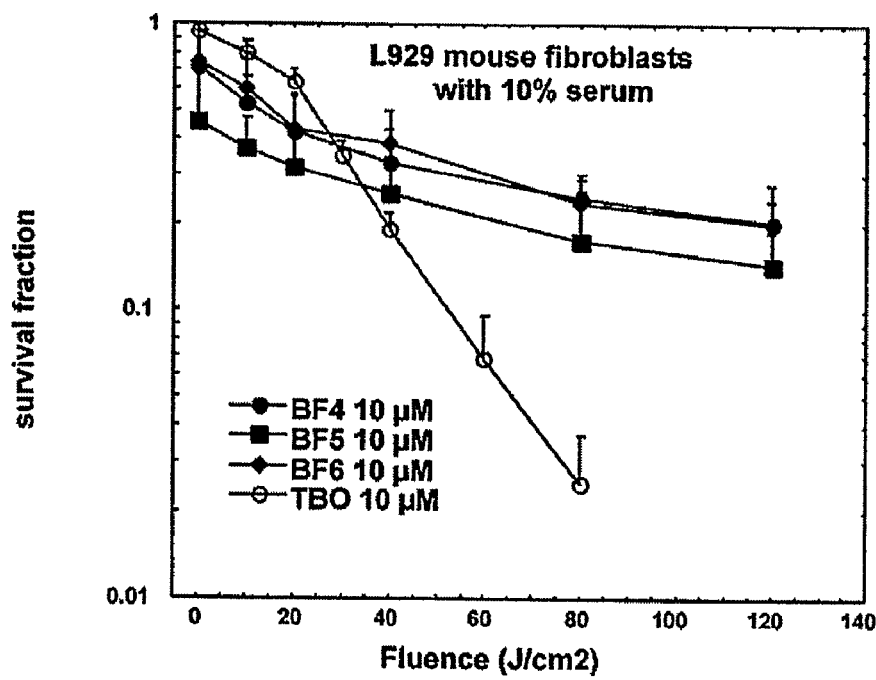

The results of this experiment are shown in FIG. 21A, and are compared with results from mammalian fibroblasts in FIG. 21B. More particularly FIG. 21 shows a comparison of PDI of *E. coli* and L929 fibroblasts incubated with either CI1-3 or TBO *E. coli* was incubated fullerenes CI1-3 or TBO under the conditions described and illumination with white or red light, respectively (FIG. 21A).

Referring to FIG. 21A, it is seen that TBO was almost ineffective in mediating PDI of *E. coli* under these conditions. When the CI1-3 mediated killing of *E. coli* under these conditions is compared with that shown in FIG. 19B (i.e., with no serum), it is seen that the effectiveness of CI1 was unchanged, whereas the killing mediated by CI2 and CI3 was reduced by about 1 log in the presence of serum (compare FIGS. 19B, 21A).

Other experiments testing other microorganisms showed that TBO at the same concentration and fluence as was used for the fullerenes (i.e., 1 µM for *S. aureus* and 10 µM for both *P. aeruginosa* and *C. albicans*) produced less than 1 log of killing in the presence or absence of serum.

The above studies were performed in order to make comparisons between the effectiveness and selectivity of the cationic fullerenes with an established antimicrobial PS, i.e., the phenothiazinium dye TBO under the same conditions. As discussed, TBO has been widely used to kill multiple classes of microbes in vitro after illumination with red light (Matevski, D., Weersink, R., Tenenbaum, H. C., Wilson, B., Ellen, R. P., and Lepine, G. (2003). Lethal photosensitization of periodontal pathogens by a red-filtered Xenon lamp in vitro. *J. Periodontal Res.* 38, 428-435, 52. Romanova, N. A., Brovko, L. Y., Moore, L., Pometun, E., Savitsky, A. P., Ugarova, N. N., and Griffiths, M. W. (2003). Assessment of photodynamic destruction of *Escherichia coli* O157:H7 and *Listeria monocytogenes* by using ATP bioluminescence. *Appl. Environ. Microbiol.* 69, 6393-6398, Soukos, N. S., Wilson, M., Burns, T., and Speight, P. M. (1996). Photodynamic effects of toluidine blue on human oral keratinocytes and fibroblasts and *Streptococcus sanguis* evaluated in vitro. *Lasers Surg. Med.* 18, 253-259, Usacheva, M. N., Teichert, M. C., and Biel, M. A. (2001). Comparison of the methylene blue and toluidine blue photobactericidal efficacy against Gram-positive and Gram-negative microorganisms. *Lasers Surg. Med.* 29, 165-173, and Wilson, M. (2004). Lethal photosensitisation of oral bacteria and its potential application in the photodynamic therapy of oral infections. *Photochem. Photobiol. Sci.* 3, 412-418). It has also been tested in several animal models of localized infections. Wong et al. (Wong, T. W., Wang, Y. Y., Sheu, H. M., and Chuang, Y. C. (2005). Bactericidal effects of toluidine blue-mediated photodynamic action on *Vibrio vulnificus*. *Antimicrob. Agents Chemother.* 49, 895-902) used topical TBO and red light to cure an otherwise fatal wound infection with *Vibrio anguillarum* in mice, Komerik et al. (Komerik, N., Nakanishi, H., MacRobert, A. J., Henderson, B., Speight, P., and Wilson, M. (2003). In vivo killing of Porphyromo-nasgingivalis by toluidine blue-mediated photosensitization in an animal model. *Antimicrob. Agents Chemother.* 47, 932-940) used TBO and light to treat a rat model of periodontal infection, and Teichert et al. (Teichert, M. C., Jones, J. W., Usacheva, M. N., and Biel, M. A. (2002). Treatment of oral candidiasis with methylene blue-mediated photodynamic therapy in an immunodeficient murine model. *Oral Surg. Oral Med. Oral Pathol. Oral Radiol. Endod.* 93, 155-160) used the closely related phenothiazinium dye methylene blue combined with light to treat a mouse model of oral candidiasis.

In these studies, TBO (under the same conditions as cationic fullerenes, i.e., 1 or 10 µM, 10 min incubation, and up to 16 J/cm2 of red light) did not kill more than 90% of any of the microbial species. Therefore, these studies show that exemplary cationic fullerenes CI2 and CI3 are many orders of magnitude more effective as antimicrobial agents than TBO, a widely used antimicrobial PS.

Example 15

Cationic Fullerenes Selectivity Kill Microbes and Spare Healthy Cells

In order to assess the selectivity of light-mediated killing of microbes over mammalian cells, mouse L929 fibroblasts were incubated with CI1-3 and with TBO under the same conditions (i.e., 10 µM concentration for 10 min in 10% FBS with a wash), followed by delivery of white or red light, respectively, up to 120 J/cm².

Results of this study are shown in FIG. 21B, and contrasted with the results for *E. coli* shown in FIG. 21A. Referring to FIG. 21B, CI1-3 did show some dark toxicity (20%-60% killing) and some additional phototoxicity (20%-30%) toward L929 cells. However, TBO displayed a different shape of killing curve, with little dark toxicity but a pronounced light-dependent toxicity, until the limit of the viability assay was reached at 80 J/cm².

To employ antimicrobial PS to treat localized infections in animals or patients, it is necessary to address the question of selectivity of the PS for microbial cells as compared to host mammalian cells, as was done in the above-described experiments. This selectivity may be relatively easy to demonstrate because antimicrobial PDI is often carried out with relatively short incubation times (minutes) before illumination, whereas mammalian cells in tissue culture are frequently incubated with PS for periods of hours (even 24 hr). Hence, if killing is compared between microbes and mammalian cells after a short incubation time, it is likely to favor microbial killing.

Another difficulty in comparisons between killing microbes and mammalian cells depends upon differences in the viability assays employed in each case. The CFU assay for microorganisms can detect 6 logs of killing, whereas the MTT assay for mammalian cell viability has a maximum detection limit of 2 logs of killing. These differences in assay methods notwithstanding, it is nevertheless clear from the data presented herein that the fullerenes show a greater level of selectivity for microbes over mammalian cells than is observed for TBO under the same conditions (FIG. 21B).

Example 16

Design of Fullerene-Based Antimicrobial Photosensitizers

The effectiveness of various photosensitizers (PS) considered for antimicrobial PDT can be judged on several criteria. Preferably the PS are able to kill multiple classes of microbes at relatively low PS concentrations and low fluences of light. PS should be reasonably nontoxic in the dark and should demonstrate selectivity for microbial cells over mammalian cells. PS should ideally have large extinction coefficients in the red part of the spectrum.

As disclosed herein, cationic fullerenes fulfill many of these criteria. As shown in FIG. 1, the fullerenes have broad absorption in the UV range, with a tail that extends well into the visible spectrum (to 550 nm in the case of CI1). The UV absorption decreases as the number of substituents on the fullerene is increased, and, consequently, the degree of conjugation is decreased. TBO, however, like many other PS used for PDT and PDI, has an absorption peak in the red at 635 nm. Many reports show that PDT in vivo is more effective with red light and near infrared light, as both the absorption and scattering of light by tissue decrease as the wavelength increases (Anderson, R. R., and Parrish, J. A. (1981). The optics of human skin. *J. Invest. Dermatol.* 77, 13-19). A broad-band pass filter that gives an output of the entire visible spectrum (400-700 nm) was used to excite the fullerenes that maximized the absorption by the tail in the visible range. UV light was not used to excite the fullerenes, as UV light is highly germicidal and can kill most microorganisms. FIG. 1 shows that the effective absorption of the delivered wavelength ranges was not very different between the fullerenes and TBO.

Screening experiments carried out against *S. aureus* at a 100 µM concentration show that a $C_{60}$ fullerene series substituted with pyrrolidinium groups (exemplified by compounds CI1-3) behaves very differently from a $C_{60}$ series substituted with di-serinol groups (exemplified by compounds NI1-3). The cationic fullerenes give high levels of dark toxicity (except for CI1), whereas the di-serinol-functionalized $C_{60}$ show a typical loss of colony-forming ability that is light dose-dependent. However, cationic fullerenes were highly effective PS at lower concentrations. This finding agrees with reports that PS with one (or preferably more) cationic groups are efficient antimicrobial PS (Hamblin, M. R., and Hasan, T. (2004). Photodynamic therapy: a new antimicrobial approach to infectious disease? *Photo-chem. Photobiol. Sci.* 3, 436-450, Minnock, A., Vernon, D. I., Schofield, J., Griffiths, J., Parish, J. H., and Brown, S. B. (1996). Photoinactivation of bacteria. Use of a cationic water-soluble zinc phthalocyanine to photoinactivate both Gram-negative and Gram-positive bacteria. *J. Photochem. Photobiol. B* 32, 159-164, Merchat, M., Bertolini, G., Giacomini, P., Villanueva, A., and Jori, G. (1996). Meso-substituted cationic porphyrins as efficient photosensitizers of Gram-positive and Gram-negative bacteria. *J. Photochem. Photobiol. B* 32, 153-157, Demidova, T. N., and Hamblin, M. R. (2004). Photodynamic therapy targeted to pathogens. *Int. J. Immunopathol. Pharmacol.* 17, 245-254, Demidova, T. N., and Hamblin, M. R. (2005). Effect of cell-photo-sensitizer binding and cell density on microbial photoinactivation. *Antimicrob. Agents Chemother.* 49, 2329-2335). Quaternary nitrogen-based groups are superior to primary, secondary, or tertiary amino groups, as the positive charge is less dependent on the pH of the surrounding media, or the pKa of the molecules with which the PS is interacting.

Microbial cells possess overall negative charges, and it is thought that cationic PS bind to these groups on the outer layers of the cell surface. Gram-positive and fungal cells have relatively permeable outer layers of peptidoglycan and lipoteichoic acid or β-glucan, respectively, although the mannan layer of *Candida* species can present a permeability barrier. This permeability allows cationic, and to a lesser extent, noncationic PS to diffuse inward to the plasma membrane, a site at which the generation of reactive oxygen species under illumination can damage the membrane structure, allowing for leakage of essential components and causing cell death. Our finding that NI1-3 are equally effective against the gram-positive *S. aureus* with and without a wash demonstrates that the neutrally charged fullerenes are indeed able to penetrate to a sufficient extent into the cell that they can not easily be washed out.

By contrast, gram-negative bacteria have a double membrane structure that presents a barrier to diffusion of many PS. Cationic compounds such as CI1-3 are able to displace divalent cations ($Ca^{2+}$ and $Mg^{2+}$) that play a role in the attachment of lipopolysaccharide to the outer membrane (Lambrechts, S. A., Aalders, M. C., Langeveld-Klerks, D. H., Khayali, Y., and Lagerberg, J. W. (2004). Effect of monovalent and divalent cations on the photoinactivation of bacteria with meso-substituted cationic porphyrins. *Photochem. Photobiol.* 79, 297-302). Such displacement is thought to weaken the structure of the outer permeability, allowing the PS to penetrate further in a process that has been termed "self-promoted uptake" (Hancock, R. E., and Bell, A. (1988). Antibiotic uptake into Gram-negative bacteria. *Eur. J. Clin. Microbiol. Infect. Dis.* 7, 713-720).

In this disclosure it has been shown inter alia that bis- and tris-cationic fullerenes are highly active antimicrobial PS that mediate the destruction of a broad spectrum of microbial classes and show better selectivity for microbes over mammalian cells than TBO, a widely used antimicrobial PS. Accordingly, functionalized fullerenes, and preferably cationic fullerenes, hold great promise as effective antimicrobial photosensitizers, particularly in those situations in which red light activation is not important for the light to penetrate deep into tissue.

Those skilled in the art will recognize, or be able to ascertain using no more than routine experimentation, many equivalents to the specific embodiments of the invention described herein. Such equivalents are intended to be encompassed by the following claims. All references disclosed herein are incorporated by reference in their entirety.

REFERENCES

It is believed that a review of the following references will appreciate understanding of the present invention. Some of these documents are referred to throughout the present disclosure by a number, as indicated below.

1. Kroto, H. W., Heath, J. R., O'Brien, S. C., Curl, R. F., and Smalley, R. E. (1985). C60: Buckminsterfullerene. Nature 318, 162-163.
2. Jensen, A. W., Wilson, S. R., and Schuster, D. I. (1996). Biological applications of fullerenes. Bioorg. Med. Chem. 4, 767-779.
3. Bosi, S., Da Ros, T., Spalluto, G., and Prato, M. (2003). Fullerene derivatives: an attractive tool for biological applications. Eur. J. Med. Chem. 38, 913-923.
4. Dugan, L. L., Lovett, E. G., Quick, K. L., Lotharius, J., Lin, T. T., and O'Malley, K. L. (2001). Fullerene-based antioxidants and neurodegenerative disorders. Parkinsonism Relat. Disord. 7, 243-246.
5. Tagmatarchis, N., and Shinohara, H. (2001). Fullerenes in medicinal chemistry and their biological applications. Mini Rev. Med. Chem. 1, 339-348.
6. Brettreich, M., and Hirsch, A. (1998). A highly water-soluble dendro[60]fullerene. Tetrahedron Lett. 39, 2731-2734.
7. Da Ros, T., Prato, M., Novello, F., Maggini, M., and Banfi, E. (1996). Easy access to water-soluble fullerene derivatives via 1,3-dipolar cycloadditions of azomethine ylides to C(60). J. Org. Chem. 61, 9070-9072.
8. Foley, S., Crowley, C., Smaihi, M., Bonfils, C., Erlanger, B. F., Seta, P., and Larroque, C. (2002). Cellular localisation of a water-soluble fullerene derivative. Biochem. Biophys. Res. Commun. 294, 116-119.
9. Bosi, S., Da Ros, T., Spalluto, G., Balzarini, J., and Prato, M. (2003). Synthesis and anti-HIV properties of new water-soluble bis-functionalized[60]fullerene derivatives. Bioorg. Med. Chem. Lett. 13, 4437-4440.
10. Schinazi, R. F., Sijbesma, R., Srdanov, G., Hill, C. L., and Wudl, F. (1993). Synthesis and virucidal activity of a water-soluble, configurationally stable, derivatized C60 fullerene. Antimicrob. Agents Chemother. 37, 1707-1710.
11. Tsao, N., Luh, T. Y., Chou, C. K., Wu, J. J., Lin, Y. S., and Lei, H. Y. (2001). Inhibition of group A *streptococcus* infection by carboxyfullerene. Antimicrob. Agents Chemother. 45, 1788-1793.
12. Dugan, L. L., Gabrielsen, J. K., Yu, S. P., Lin, T. S., and Choi, D. W. (1996). Buckminsterfullerenol free radical scavengers reduce excitotoxic and apoptotic death of cultured cortical neurons. Neurobiol. Dis. 3, 129-135.
13. Jin, H., Chen, W. Q., Tang, X. W., Chiang, L. Y., Yang, C. Y., Schloss, J. V., and Wu, J. Y. (2000). Polyhydroxylated C(60), fullerenols, as glutamate receptor antagonists and neuroprotective agents. J. Neurosci. Res. 62, 600-607.
14. Tsai, M. C., Chen, Y. H., and Chiang, L. Y. (1997). Polyhydroxylated C60, fullerenol, a novel free-radical trapper, prevented hydrogen peroxide- and cumene hydroperoxide-elicited changes in rat hippocampus in-vitro. J. Pharm. Pharmacol. 49, 438-445.
15. Mashino, T., Nishikawa, D., Takahashi, K., Usui, N., Yamori, T., Seki, M., Endo, T., and Mochizuki, M. (2003). Antibacterial and antiproliferative activity of cationic fullerene derivatives. Bioorg. Med. Chem. Lett. 13, 4395-4397.
16. Mashino, T., Usui, N., Okuda, K., Hirota, T., and Mochizuki, M. (2003). Respiratory chain inhibition by fullerene derivatives: hydrogen peroxide production caused by fullerene derivatives and a respiratory chain system. Bioorg. Med. Chem. 11, 1433-1438.
17. Mashino, T., Shimotohno, K., Ikegami, N., Nishikawa, D., Okuda, K., Takahashi, K., Nakamura, S., and Mochizuki, M. (2005). Human immunodeficiency virus-reverse transcriptase inhibition and hepatitis C virus RNA-dependent RNA polymerase inhibition activities of fullerene derivatives. Bioorg. Med. Chem. Lett. 15, 1107-1109.
18. Castano, A. P., Demidova, T. N., and Hamblin, M. R. (2004). Mechanisms in photodynamic therapy: part one-photosensitizers, photochemistry and cellular localization. Photodiag. Photodyn. Ther. 1, 279-293.
19. Yamakoshi, Y., Umezawa, N., Ryu, A., Arakane, K., Miyata, N., Goda, Y., Masumizu, T., and Nagano, T. (2003). Active oxygen species generated from photoexcited fullerene (C60) as potential medicines: O2-* versus 1O2. J. Am. Chem. Soc. 125, 12803-12809.
20. Liu, Y., Zhao, Y. L., Chen, Y., Liang, P., and Li, L. (2005). A water-soluble bcyclodextrin derivative possessing a fullerene tether as an efficient photodriven DNA-cleavage reagent. Tetrahedron Lett. 46, 2507-2511.
21. Kasermann, F., and Kempf, C. (1997). Photodynamic inactivation of enveloped viruses by buckminsterfullerene. Antiviral Res. 34, 65-70.
22. Sera, N., Tokiwa, H., and Miyata, N. (1996). Mutagenicity of the fullerene C60-generated singlet oxygen dependent formation of lipid peroxides. Carcinogenesis 17, 2163-2169.
23. Burlaka, A. P., Sidorik, Y. P., Prylutska, S. V., Matyshevska, O. P., Golub, O. A., Prylutskyy, Y. I., and Scharff, P. (2004). Catalytic system of the reactive oxygen species on the C60 fullerene basis. Exp. Oncol. 26, 326-327.
24. Tabata, Y., Murakami, Y., and Ikada, Y. (1997). Photodynamic effect of polyethylene glycol-modified fullerene on tumor. Jpn. J. Cancer Res. 88, 1108-1116.
25. Moan, J., and Peng, Q. (2003). An outline of the hundred-year history of PDT. Anticancer Res. 23, 3591-3600.
26. Dolmans, D. E., Fukumura, D., and Jain, R. K. (2003). Photodynamic therapy for cancer. Nat. Rev. Cancer 3, 380-387.
27. Brown, S. B., and Mellish, K. J. (2001). Verteporfin: a milestone in opthalmology and photodynamic therapy. Expert Opin. Pharmacother. 2, 351-361.
28. Wainwright, M. (1998). Photodynamic antimicrobial chemotherapy (PACT). J. Antimicrob. Chemother. 42, 13-28.
29. Maisch, T., Szeimies, R. M., Jori, G., and Abels, C. (2004). Antibacterial photodynamic therapy in dermatology. Photochem. Photobiol. Sci. 3, 907-917.

30. Hamblin, M. R., and Hasan, T. (2004). Photodynamic therapy: a new antimicrobial approach to infectious disease? Photo-chem. Photobiol. Sci. 3, 436-450.

31. Minnock, A., Vernon, D. I., Schofield, J., Griffiths, J., Parish, J. H., and Brown, S. B. (1996). Photoinactivation of bacteria. Use of a cationic water-soluble zinc phthalocyanine to photoinactivate both Gram-negative and Gram-positive bacteria. J. Photochem. Photobiol. B 32, 159-164.

32. Nitzan, Y., Dror, R., Ladan, H., Malik, Z., Kimel, S., and Gottfried, V. (1995). Structure-activity relationship of porphines for photoinactivation of bacteria. Photochem. Photobiol. 62, 342-347.

33. Merchat, M., Bertolini, G., Giacomini, P., Villanueva, A., and Jori, G. (1996). Meso-substituted cationic porphyrins as efficient photosensitizers of Gram-positive and Gram-negative bacteria. J. Photochem. Photobiol. B 32, 153-157.

34. Minnock, A., Vernon, D. I., Schofield, J., Griffiths, J., Parish, J. H., and Brown, S. B. (2000). Mechanism of uptake of a cationic water-soluble pyridinium zinc phthalocyanine across the outer membrane of Escherichia coli. Antimicrob. Agents Chemother. 44, 522-527.

35. Wharton, T., Kini, V. U., Mortis, R. A., and Wilson, L. J. (2001). New non-ionic, highly water-soluble derivatives of C60 designed for biological compatibility. Tetrahedron Lett. 42, 5159-5162.

36. Wharton, T., and Wilson, L. J. (2002). Highly-iodinated fullerene as a contrast agent for X-ray imaging. Bioorg. Med. Chem. 10, 3545-3554.

37. Maggini, M., Scorrano, G., and Prato, M. (1993). Addition of azomethine ylides to C60: synthesis, characterization, and functionalization of fullerene pyrrolidines. J. Am. Chem. Soc. 115, 9798-9799.

38. Cassell, A. M., Scrivens, W. A., and Tour, J. M. (1998). Assembly of DNA/fullerene hybrid materials. Angew. Chem. Int. Ed. Engl. 37, 1528-1530.

39. Malik, Z., Ladan, H., and Nitzan, Y. (1992). Photodynamic inactivation of Gram-negative bacteria: problems and possible solutions. J. Photochem. Photobiol. B 14, 262-266.

40. Nitzan, Y., Gutterman, M., Malik, Z., and Ehrenberg, B. (1992). Inactivation of Gram-negative bacteria by photosensitized porphyrins. Photochem. Photobiol. 55, 89-96.

41. Wilson, M., and Pratten, J. (1995). Lethal photosensitisation of Staphylococcus aureus in vitro: effect of growth phase, serum, and pre-irradiation time. Lasers Surg. Med. 16, 272-276.

42. Lambrechts, S. A., Aalders, M. C., Verbraak, F. D., Lager-berg, J. W., Dankert, J. B., and Schuitmaker, J. J. (2005). Effect of albumin on the photodynamic inactivation of microorganisms by a cationic porphyrin. J. Photochem. Photobiol. B 79, 51-57.

43. Anderson, R. R., and Parrish, J. A. (1981). The optics of human skin. J. Invest. Dermatol. 77, 13-19.

44. Demidova, T. N., and Hamblin, M. R. (2004). Photodynamic therapy targeted to pathogens. Int. J. Immunopathol. Pharmacol. 17, 245-254.

45. Demidova, T. N., and Hamblin, M. R. (2005). Effect of cell-photo-sensitizer binding and cell density on microbial photoinactivation. Antimicrob. Agents Chemother. 49, 2329-2335.

46. Lambrechts, S. A., Aalders, M. C., Langeveld-Klerks, D. H., Khayali, Y., and Lagerberg, J. W. (2004). Effect of monovalent and divalent cations on the photoinactivation of bacteria with meso-substituted cationic porphyrins. Photochem. Photobiol. 79, 297-302.

47. Hancock, R. E., and Bell, A. (1988). Antibiotic uptake into Gram-negative bacteria. Eur. J. Clin. Microbiol. Infect. Dis. 7, 713-720.

48. Mashino, T., Okuda, K., Hirota, T., Hirobe, M., Nagano, T., and Mochizuki, M. (1999). Inhibition of E. coli growth by fullerene derivatives and inhibition mechanism. Bioorg. Med. Chem. Lett. 9, 2959-2962.

49. Hancock, R. E., and Wong, P. G. (1984). Compounds which increase the permeability of the Pseudomonas aeruginosa outer membrane. Antimicrob. Agents Chemother. 26, 48-52.

50. Hancock, R. E. (1986). Intrinsic antibiotic resistance of Pseudomonas aeruginosa. J. Antimicrob. Chemother. 18, 653-656.

51. Matevski, D., Weersink, R., Tenenbaum, H. C., Wilson, B., Ellen, R. P., and Lepine, G. (2003). Lethal photosensitization of periodontal pathogens by a red-filtered Xenon lamp in vitro. J. Periodontal Res. 38, 428-435.

52. Romanova, N. A., Brovko, L. Y., Moore, L., Pometun, E., Savitsky, A. P., Ugarova, N. N., and Griffiths, M. W. (2003). Assessment of photodynamic destruction of Escherichia coli O157:H7 and Listeria monocytogenes by using ATP bioluminescence. Appl. Environ. Microbiol. 69, 6393-6398.

53. Soukos, N. S., Wilson, M., Burns, T., and Speight, P. M. (1996). Photodynamic effects of toluidine blue on human oral keratinocytes and fibroblasts and Streptococcus sanguise valuated in vitro. Lasers Surg. Med. 18, 253-259.

54. Usacheva, M. N., Teichert, M. C., and Biel, M. A. (2001). Comparison of the methylene blue and toluidine blue photobactericidal efficacy against Gram-positive and Gram-negative microorganisms. Lasers Surg. Med. 29, 165-173.

55. Wilson, M. (2004). Lethal photosensitisation of oral bacteria and its potential application in the photodynamic therapy of oral infections. Photochem. Photobiol. Sci. 3, 412-418.

56. Wong, T. W., Wang, Y. Y., Sheu, H. M., and Chuang, Y. C. (2005). Bactericidal effects of toluidine blue-mediated photodynamic action on Vibrio vulnificus. Antimicrob. Agents Chemother. 49, 895-902.

57. Komerik, N., Nakanishi, H., MacRobert, A. J., Henderson, B., Speight, P., and Wilson, M. (2003). In vivo killing of Porphyromo nasgingivalis by toluidine blue-mediated photosensitization in an animal model. Antimicrob. Agents Chemother. 47, 932-940.

58. Teichert, M. C., Jones, J. W., Usacheva, M. N., and Biel, M. A. (2002). Treatment of oral candidiasis with methylene blue-mediated photodynamic therapy in an immunodeficient murine model. Oral Surg. Oral Med. Oral Pathol. Oral Radiol. Endod. 93, 155-160.

59. Chen, Y. W., Hwang, K. C., Yen, C. C., and Lai, Y. L. (2004). Fullerene derivatives protect against oxidative stress in RAW 264.7 cells and ischemia-reperfused lungs. Am. J. Physiol. Regul. Integr. Comp. Physiol. 287, R21-R26.

60. Taylor, A. E. (2004). Fullerene derivatives protect against oxidative stress in murine macrophage line cells and ischemia-reper-fused lungs. Am. J. Physiol. Regul. Integr. Comp. Physiol. 287, R1-R2.

61. Hamano, T., Okuda, K., Mashino, T., Hirobe, M., Arakane, K., Ryu, A., Mashiko, S., and Nagano, T. (1997). Singlet oxygen production from fullerene derivatives: effect of sequential functionalization of the fullerene core. Chem. Commun. 21-22.

62. Jett, B. D., Hatter, K. L., Huycke, M. M., and Gilmore, M. S. (1997). Simplified agar plate method for quantifying viable bacteria. Biotechniques 23, 648-650.

63. Earle, W. R., Schilling, E. L., Stark, T. H., Straus, N. P., Brown, M. F., and Shelton, E. (1943). Production of malignancy in vitro. IV. The mouse fibroblast cultures and changes seen in the living cells. J. Natl. Cancer Inst. 4, 165-212.

64. Merlin, J. L., Azzi, S., Lignon, D., Ramacci, C., Zeghari, N., and Guillemin, F. (1992). MTT assays allow quick and reliable measurement of the response of human tumour cells to photodynamic therapy. Eur. J. Cancer 28A, 1452-1458.

What is claimed is:

1. A functionalized fullerene compound of the formula:

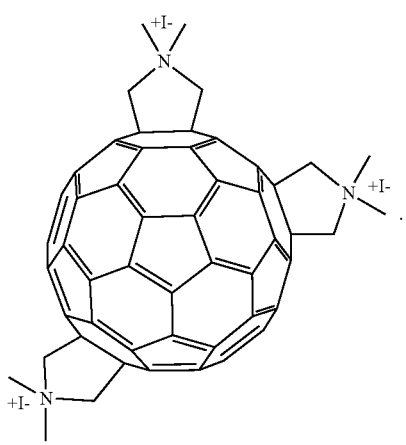

2. A pharmaceutical composition, comprising:

a biocompatible carrier and an effective amount of a functionalized fullerene compound of claim 1.

3. The pharmaceutical composition of claim 2, wherein the composition is a solution having a fullerene concentration of between 1 and 100 micromolar.

4. The composition of claim 2, further comprising a hyperosmotically active chemical species.

* * * * *